US008630874B2

(12) United States Patent
Kusens

(10) Patent No.: US 8,630,874 B2
(45) Date of Patent: Jan. 14, 2014

(54) PREVENTIVE CARE ENGINE

(71) Applicant: Intermedhx, LLC, North Miami Beach, FL (US)

(72) Inventor: Bruce Howard Kusens, North Miami Beach, FL (US)

(73) Assignee: Intermedhx, LLC, North Miami Beach, FL (US)

( * ) Notice: Subject to any disclaimer, the term of this patent is extended or adjusted under 35 U.S.C. 154(b) by 0 days.

(21) Appl. No.: 13/668,051

(22) Filed: Nov. 2, 2012

(65) Prior Publication Data

US 2013/0117038 A1 May 9, 2013

Related U.S. Application Data

(60) Provisional application No. 61/557,068, filed on Nov. 8, 2011.

(51) Int. Cl.
*G06Q 10/00* (2012.01)
(52) U.S. Cl.
USPC .................................................. 705/2; 705/3
(58) Field of Classification Search
USPC ............................................................. 705/2
See application file for complete search history.

(56) References Cited

U.S. PATENT DOCUMENTS

| 7,698,154 | B2 | 4/2010 | Marchosky | |
|---|---|---|---|---|
| 8,321,241 | B1 | 11/2012 | Mansour et al. | |
| 2002/0010597 | A1* | 1/2002 | Mayer et al. | 705/2 |
| 2002/0132664 | A1 | 9/2002 | Miller et al. | |
| 2004/0024749 | A1 | 2/2004 | Kusens | |
| 2005/0215315 | A1 | 9/2005 | Miller et al. | |
| 2007/0016450 | A1 | 1/2007 | Bhora et al. | |
| 2010/0324934 | A1* | 12/2010 | Selinfreund et al. | 705/3 |
| 2012/0203576 | A1 | 8/2012 | Bucur et al. | |

* cited by examiner

*Primary Examiner* — Hiep V Nguyen
(74) *Attorney, Agent, or Firm* — Kilpatrick Townsend & Stockton LLP

(57) ABSTRACT

A preventative care recommendation engine to provide a preventative care recommendation corresponding to a patient is disclosed. Processor(s) may be coupled to network interface(s) accessible by healthcare provider(s) and/or patient(s), to execute instructions to access a set of confidential health information for an identified patient, where the set is derived from a first data source, and includes an indication of a health condition of the identified patient, a healthcare service provided to the identified patient, and/or a time when the health care service was provided to the identified patient. A second data source that includes a set of criteria specified by a third party indicating a preventative care service may be accessed. A recommendation corresponding to the identified patient may be sent, wherein the recommendation is a function of the set of confidential health information for the identified patient and the set of criteria.

11 Claims, 17 Drawing Sheets

200

REPORT: ANA PATIENT

Comments:

202 {
- Personal Profile
  - Name: ANA Patient
  - Address: 2001 S RD APT XX , FL
  - Home Phone Number: 305-NNN-1234
  - Email Address: bxxxxxms@xxxsite.com
  - Height:
  - Weight:
  - Blood Type:
  - Gender: Female
  - DOB: 12/07/19XX
  - Part A Effective Date: 12/01/1991
  - Part B Effective Date: 12/01/1991

204 {
- Emergency Contact
  - You have not entered information for this section.
- Self Reported Medical Conditions
  - You have not entered information for this section.
- Self Reported Allergies
  - You have not entered information for this section.
- Self Reported Implantable Devices
  - You have not entered information for this section.
- Family Medical History
  - You have not entered information for this section.

204 {
Drugs
You have not entered information for this section.

206 {
Preventive Services

*Denotes Services that you are overdue for an appointment

| Name | Eligibility Date |
|---|---|
| *DIABETES | 13/01/1991 |
| *PAP TEST DR | 13/01/1991 |
| *PELVIC | 13/01/1991 |
| *PAP TEST | 10/01/1999 |
| *CARDIOVASCULAR | 01/01/2005 |
| *MAMMOGRAPHY | 01/01/2005 |
| *ABDOMINAL AORTIC ANEURYSM | 07/01/2007 |
| *ANNUAL WELLNESS VISIT | 01/01/2011 |
| *COLORECTAL | 02/01/2012 |
| *PPV | |
| *SMOKING CESSATION (counseling to stop smoking) | |

204 {
Providers
You have not entered information for this section.

Pharmacies
You have not entered information for this section.

208 {
- Plans and Coverage
- Medicare Health & Prescription Drug Plans

| Plan Name | Plan Type | Plan Period |
|---|---|---|
| S5820-010 | 11 - Medicare Prescription Drug Plan | 01/01/2006 - current |

Other Insurance

| Insurer Name Policy Number | Insurer Address | COBA ID | Coverage Dates |
|---|---|---|---|
| AMERICAN INSURANCE CO. Policy No.: | 12345 S. 200 E. ORLANDO, FL 32801 | 30034 | 12/01/1992 - current |

204 {
- Self Reported Immunization
  - You have not entered information for this section.
- Self-Report Lab Tests and Results
  - You have not entered information for this section.
- Self Reported Vital Statistics
  - You have not entered information for this section.

FIG. 2C

PREVENTIVE CARE ENGINE

This application claims benefit of and priority to U.S. Provisional Application No. 61/557,068, filed Nov. 8, 2011, entitled "Preventive Care Reminder System," and is entitled to that filing date for priority. The specification, figures and complete disclosure of U.S. Provisional Application No. 61/557,068 are incorporated herein by specific reference for all purposes.

BACKGROUND

This disclosure relates in general to health information, but not by way of limitation, to health information under regulatory control and preventative care services amongst other things.

In the current environment, healthcare spending in the United States accounts for over 17% of the GDP according to a 2009 report by the Organization for Economic Co-operation and Development (OECD), and healthcare spending has increased over the past few years. While there are many factors involved in this increase of healthcare costs, experts agree that a major factor in the rising costs is a lack of preventive care in the country. In addition to increasing costs due to a lack of preventive care, a 2007 study released by The National Commission on Prevention Priorities concluded that hundreds of thousands of deaths could be prevented each year through the use of preventive care. Other reports have reached similar conclusions regarding preventive care.

The U.S. Preventive Services Task Force (Task Force) propagates preventive care recommendations for primary care clinicians and health care systems. The recommendations are outlined according to a coding method, where a given recommendation is assigned a letter grade, such as A, B, C, etc. A particular grade assigned to a particular preventive care service may indicate the Task Force's assessment of the service. For example, a grade of "A" may indicate a relatively stronger recommendation for a particular preventive care service, indicating that the service may possess a high certainty of benefit to a patient. The recommendations can be calendar-based or require some medical judgment. Grade levels A and B, for example, may entail fairly mechanical qualifications, such as an amount of time since a particular test or therapy was last performed on a particular patient. Thus, proper recommendations for preventive care for the particular patient can depend on the quality of patient records.

However, the current state of medical records, generally, is fraught with inconsistencies, inaccuracies, isolations, and other difficulties. Many medical records are handwritten or isolated on data islands maintained by a provider, a payer, or a governmental agency. Unlike some other countries, the United States has no national health care identifier; newborns and some residents do not have Social Security numbers; and patients may change away from their maiden names, use nicknames, or use other name variations when interacting in various healthcare pockets. All this contributes to inaccurate and fragmented records. As a result, patients and healthcare providers can lack awareness of preventive care options. There is a need in the health care sector to address these and other related problems.

SUMMARY

In one embodiment, health information is consolidated. The health information may be confidential, under regulatory control, and/or related to a particular patient. The health information may be from manifold sources. Healthcare payers, which may include Medicare and/or insurance companies, for non-limiting example, may be sources of health information. Healthcare providers, which may include physicians and/or clinicians, for non-limiting example, may be sources of health information. Patients may be sources of health information in some cases. Additionally, there may be other sources, such as immunization registries and/or health information exchanges. The consolidation of the heath information from the sources may include organizing, categorizing, qualifying, and/or comparing sets of information; detecting, identifying, and/or handling errors/discrepancies; and/or otherwise processing the sets of confidential health information for the patient. The consolidated information may be stored in repository and made accessible to authorized users through a health information portal. The authorized users may include one or more of the patient, the patient's healthcare provider, and/or the patient's healthcare payer.

In another embodiment, integrity of health information is checked. Anomalies may be spotted, for non-limiting example, identifying gaps in information, conflicting information, impossible/improbable information, and/or similar records that may be related. Naming and identification issues can be solved by linking together datasets that do not exactly match. An algorithm may take into account age, geography, address, and/or other factors that can be used to identify similar records that might be linked together. Prompted by flagging in some cases, the provider and/or, under some circumstances, the patient can correct errors and add additional information. This error correction can be provisioned in a way that obscures protected information to maintain confidentiality; and the manner of maintaining that confidentiality may be vary depending on whether the user is the patient or provider. The source of the corrections and additions can be recorded for providence.

In yet another embodiment, a preventative care recommendation corresponding to a patient is provided. The confidential health information of the patient may be compared to a set of preventive care recommendations (e.g., those propagated by the Task Force) to determine which recommendations are applicable to the patient and which recommendations may be applicable to the patient depending on medical judgment of a healthcare provider tending to the patient and/or depending on additional information that is needed to make the determination. Where additional information is required in certain circumstances, a workflow can be specified for a provider that could include a decision tree to gather information used in diagnosis with areas of medical judgment left to the provider. Any answered questions may be fed back into the medical record. Preventative care guideline information may be provided along with the information needed to comply with reimbursement eligibility. Certain eligibility is calendar-based and, with reliable medical records, can be recommended to the patient without provider preapproval. The patient may be told of services to seek and any preparation or information to provide. A similar workflow and decision tree may be provided to assure the patient is qualified and that it will be reimbursed. Providers of the specified care can be recommended based upon location, amenities, schedule, technology, etc. Recommendations could automatically include a Wiki or other explanation that explains the treatments or tests that are recommended to compile an information packet tailored to the patient or the provider. The patient could be explained why the recommendation is important and how their health may be improved with videos and other rich media explanations. The provider may be provided access to the underlying studies so that their medical judgment is enriched with the actual findings.

In still another embodiment, changes in the preventive care guidelines are handled. Providers and/or patients can be notified of those changes. Past recommendations and treatments/tests/therapies may be considered in order to correct any out-of-date information or recommendations. Text, voice, e-mail, and/or paper mail notifications could be sent only to those affected by the revisions. The e-mail could have a link back to a login to a provider/payer site and/or health information portal to get the confidential information. The patient could be sent reminders to see their primary care provider or a provider of the recommended preventive care.

In still another embodiment, a preventative care recommendation engine to provide a preventative care recommendation corresponding to a patient is disclosed. One or more network interfaces may be accessible by one or more of a healthcare provider and/or a patient. One or more processors may be coupled to the one or more network interfaces to execute instructions to access a set of confidential health information for an identified patient. The set of confidential health information for the identified patient may be derived from a first data source and may include one or more of an indication of a health condition of the identified patient, an indication of a healthcare service provided to the identified patient, and/or an indication of a time when the health care service was provided to the identified patient. A second data source that includes a set of criteria specified by a third party indicating eligibility of a preventative care service for payment by the third party may be accessed. A recommendation corresponding to the identified patient may sent. The recommendation may be a function of the set of confidential health information for the identified patient and the set of criteria specified by the third party indicating eligibility of the preventative care service for payment by the third party. One or more storage media may be coupled to the one or more processors to retain the instructions.

In still another embodiment, a method to provide a preventative care recommendation corresponding to a patient is disclosed. A set of confidential health information for an identified patient may be accessed. The set of confidential health information may be derived from a first data source and may include one or more of an indication of a health condition of the identified patient, an indication of a healthcare service provided to the identified patient, and/or an indication of a time when the health care service was provided to the identified patient. A second data source that includes a set of criteria specified by a third party indicating eligibility of a preventative care service for payment by the third party may be accessed. A recommendation corresponding to the identified patient may be sent. The recommendation may be a function of the set of confidential health information for the identified patient and the set of criteria specified by the third party indicating eligibility of the preventative care service for payment by the third party.

In still another embodiment, disclosed are one or more non-transitory machine-readable media having machine-readable instructions thereon which, when executed by one or more processors, implements a method provide a preventative care recommendation corresponding to a patient. A set of confidential health information for an identified patient may be accessed. The set of confidential health information may be derived from a first data source and may includes one or more of an indication of a health condition of the identified patient, an indication of a healthcare service provided to the identified patient, and/or an indication of a time when the health care service was provided to the identified patient. A second data source that includes a set of criteria specified by a third party indicating eligibility of a preventative care service for payment by the third party may be accessed. A recommendation corresponding to the identified patient may be sent. The recommendation may be a function of the set of confidential health information for the identified patient and the set of criteria specified by the third party indicating eligibility of the preventative care service for payment by the third party.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures:

FIGS. 2A, 2B, and 2C depict one possible non-limiting example of confidential health information that may be retained and/or available for a patient from a data source, in accordance with certain embodiments of the present disclosure;

Figure 1:
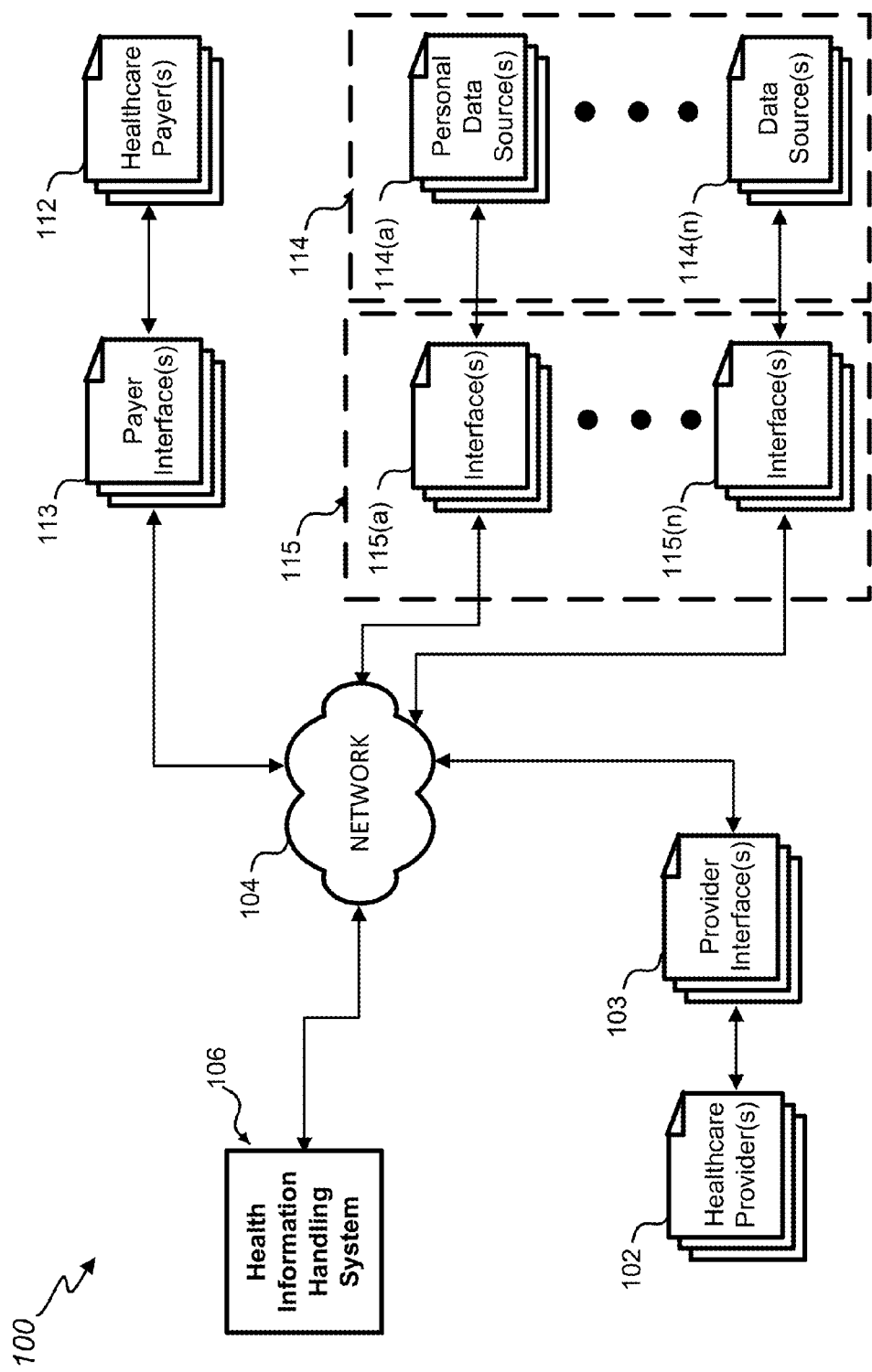
FIG. 1 depicts a high-level block diagram of a system, in accordance with certain embodiments of the present disclosure.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" (or "storage media") may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" (or "computer-readable media") includes, but is not limited to, portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Certain embodiments according the present disclosure utilize available health information to inform healthcare providers of preventive care benefits and may improve their ability provide patients with access to preventive care. Certain embodiments ensure patients are knowledgeable of preventive care benefits and able to obtain the preventive care services for which they are eligible. Certain embodiments provide significant administrative, clinical, and/or financial benefit to healthcare payers, providers and patients, including, but not limited to, reducing costs for overall medical care and reducing the number of deaths each year due to detectable and preventable medical conditions. Thus, embodiments can redound to individual benefits of patients and to the general benefit of society by promoting wellness through prevention and detection.

Certain embodiments consolidate health information to overcome the inconsistencies, inaccuracies, isolations, and other difficulties related to many medical records. Certain embodiments check integrity of health information and provide for anomaly-spotting by identifying gaps in information, conflicting information, impossible/improbable information, similar records that may be related. Certain embodiments facilitate identification of preventive care procedures that a given patient is due and/or eligible for and that are authorized for payment by healthcare payers. Certain embodiments provide recommendations regarding preventive care for healthcare providers and/or patients, and some embodiments provide for assessing and/or improving reliability of preventive care recommendations.

Various embodiments will now be discussed in greater detail with reference to the accompanying figures, beginning with FIG. 1.

FIG. 1 depicts a high-level block diagram of a system 100, in accordance with certain embodiments of the present disclosure. The system 100 allows transfer of information from and/or to a health information handling system 106, one or more healthcare providers 102, one or more healthcare payers 112, and/or one or more data sources 114. As depicted, the healthcare providers 102 may be communicatively coupled or couplable to a network 104 through one or more provider interfaces 103. The healthcare payers 112 may be communicatively coupled or couplable to the network 104 through one or more payer interfaces 113. The data sources 114 may be communicatively coupled or couplable to the network 104 through one or more data source interfaces 115.

The network 104 may be any suitable means to facilitate data transfer in the system 100. In various embodiments, the network 104 may be implemented with, without limitation, one or more of the Internet, a wide area network (WAN), a local area network (LAN), a wireless local area network (WLAN), a metropolitan area network (MAN), a cellular network, such as through 4G, 3G, GSM, etc., another wireless network, a gateway, and/or any other appropriate architecture or system that facilitates the communication of signals, data, and/or message. The network 104 may transmit data using any suitable communication protocol. The network 104 and its various components may be implemented using hardware, software, and communications media such wires, optical fibers, microwaves, radio waves, and other electromagnetic and/or optical carriers, and/or any combination of the foregoing.

The health information handling system 106 may be communicatively coupled or couplable to the network 104. In various embodiments, the health information handling system 106 may include any device or set of devices configured to compute, process, organize, categorize, qualify, send, receive, retrieve, generate, convey, store, display, present, detect, handle, and/or use any form of information and/or data suitable for embodiments described herein. The health information handling system 106 could include a single computing device, a server, for example, or multiple computing devices, which may be implemented in or with a distributed computing and/or cloud computing environment with a plurality of servers and cloud-implemented resources. Thus, the health information handling system 106 may include one or more servers. The health information handling system 106 may include one or more processing resources communicatively coupled to one or more storage media, random access memory (RAM), read-only memory (ROM), and/or other types of memory. The health information handling system 106 may include any one or combination of various input and output (I/O) devices, network ports, and display devices.

The healthcare provider(s) 102 may include an individual, an institution, and/or another entity that provides medical, preventive, curative, promotional, rehabilitative, and/or health services to patients, and/or that furnishes, bills, and/or is paid for health care in the normal course of business. The healthcare provider 102 may include without limitation, one or more of a hospital, a physician, a physician's office, a clinician, a clinic, a nurse practitioner, a physician's assistant, a specialist, an ambulatory surgery center, an assisted living facility, a nursing home, etc. In various embodiments, the healthcare provider 102 could include one or more of a database, any repository of data in any suitable form, a website, and/or a server. In certain aspects, the healthcare provider 102 may be a user of the system; in certain aspects, the healthcare provider 102 may be a source of health information about patients. By way of example without limitation, a doctor, as a healthcare provider 102, may be a user that receives information whether through the network 104 or otherwise, may provide information to the health information handling system 106 about patients, and/or may have access to records, databases, and/or other repositories containing information about patients. The doctor's information repositories may be electronically and accessibly linked to the health information handling system 106 such that the repositories may correspond to the healthcare provider 102 in some embodiments.

The healthcare provider interface(s) 103 may include for example without limitation a web interface allowing for transfer of and access to one or more of biographical information, demographic information, medical information, medical conditions, care provided, preventive care recommendation information, preventative care eligibility, payer coverage, regulatory information, etc. Healthcare providers may have web site/portals giving access to such information. The healthcare provider interface 103 may include any suitable input/output module or other system/device operable to serve as an interface between the healthcare provider 102 and the network 104. The healthcare provider interface 103 may facilitate communication over the network 104 using any suitable transmission protocol and/or standard. In some embodiments, the health information handling system 106 may include and/or provide the healthcare provider interface 103, for example, by making available one or more of a website, a web page, a web portal, a web application, a mobile application, enterprise software, and/or any suitable application software. In certain embodiments, healthcare provider interface 103 may include a mobile computing device that may be any portable device suitable for sending and receiving information over a network in accordance with embodiments described herein. For example without limitation, in various embodiments, the mobile computing device may include one or more devices variously referenced as a mobile phone, a cellular telephone, a smartphone, a handheld mobile device, a tablet computer, a web pad, a personal digital assistant (PDA), a notebook computer, a handheld computer, a laptop computer, or the like.

Certain embodiments allow the healthcare provider 102 to track a patient's health information, consolidated into one place. The healthcare provider 102 may be able to see what preventive services are recommended for a particular patient, see what preventive services are eligible for coverage by a healthcare payer, and see the extent of coverage from zero cost-sharing to cost-sharing to no coverage. The healthcare provider 102 may be able to see what preventive services may be applicable contingent upon further information to be provided by the patient 110 and/or the medical judgment of the healthcare provider 102. The healthcare provider 102 may be given explanation(s), such as a Wiki or any suitable explanation, describing preventive services, applicability of preventive services, eligibility for coverage, reimbursement guidelines that might specify what qualifying information is needed in order to determine services for which the payer will provide payment, the importance of the preventive service, any other further information needed, other potentially relevant information, etc. With some embodiments, where additional information is required in certain circumstances, a workflow can be specified for the healthcare provider 102 that could include a decision tree to gather information used in diagnosis with areas of medical judgment left to the provider. The workflow may include any one or combination of a graphical decision tree, a textual decision tree, a series of prompts configured to walk the provider through a decision tree, a flowchart, an instructional narrative, a list, and/or the like. And the provider may have the option to print the workflow. The preventative care guidelines may be provided along with the information needed to comply with reimbursement eligibility. Different payers can have different preventative care guidelines along with reimbursement eligibility such that each patient might have a customized interaction with the provider. Indications of the customized information may be provided to the healthcare provider 102. Any one or combination of the foregoing may be provided to the healthcare provider 102 through a single provider interface 103.

The healthcare payer(s) 112 may include any entity/organization/institution that provides for payment related to healthcare, healthcare services, and/or claims for healthcare services, and/or that administers insurance and/or benefits. The healthcare payer 112 may include, without limitation, one or more of a government agency/program (e.g., Medicare, Medicaid, Children's Health Insurance Program (CHIP)), an insurance company, a health care professional (HMO), preferred provider organization (PPO), an organization that may be contracted by said examples, etc. In various embodiments, the healthcare payer 112 could include one or more of a database, any repository of data in any suitable form, a website, and/or a server. In certain aspects, the healthcare payer 112 may be a user of the system; in certain aspects, the healthcare payer 112 may be a source of health information and/or payer coverage/benefit information relating to patients. By way of example without limitation, a private insurance company, as a healthcare payer 112, may be a user that receives information whether through the network 104 or otherwise, may provide information to the health information handling system 106 about patients, and/or may have access to records, databases, and/or other repositories containing information about patients. The insurer's information repositories may be electronically and accessibly linked to the health information handling system 106 such that the repositories may correspond to the healthcare payer 112 in some embodiments.

The healthcare payer interface(s) 113 may include for example without limitation a web interface allowing for transfer of and access to one or more of biographical information, demographical information, medical information, medical conditions, care provided, preventive care recommendation information, preventative care eligibility, payer coverage, regulatory information, etc. Healthcare payers may have web site/portals giving access to such information. For example, Medicare may have such a portal that can be tapped to gather information on patients of Medicare. The healthcare payer interface 113 may include any suitable input/output module or other system/device operable to serve as an interface between the healthcare payer 112 and the network 104. The healthcare payer interface 113 may facilitate communication over the network 104 using any suitable transmission protocol, standard, and/or encryption. In some embodiments, the health information handling system 106 may include and/or provide the healthcare payer interface 113, for example, by making available one or more of a website, a web page, a web portal, a web application, a mobile application, enterprise software, and/or any suitable application software.

Certain embodiments involving the one or more data source 114 may include one or more personal data sources 114(a). The personal data sources 114(a) may correspond to health information maintained/facilitated by patients and stored with one or more internet-accessible databases, repositories, and/or web site/portal. By way of non-limiting example, the personal data sources 114(a) may correspond to common platforms such as Microsoft's Health Vault™, WebMD™, and/or various health management systems that may be linked to the health information handling system 106 via the network 104 so that patient-related information retained by the personal data sources 114(a) may be accessed by/transferred to the health information handling system 106.

In various embodiments, the data sources 114 may include any number of other data sources 114(n). The data sources 114(n) may include any other suitable source whereby health information is accessible. The data sources 114(n) may provide information to the health information handling system 106 about patients, and/or may have access to records, databases, and/or other repositories containing information about patients. As a non-limiting example, some data source(s) 114(n) may correspond to one or more immunization registries. As another non-limiting example, some data source(s) 114(n) may correspond to one or more health information exchanges. As yet another non-limiting example, some data source(s) 114(n) may correspond to one or more regulatory information sources. Regulatory information may include without limitation regulations issued by a government authority, rules/guidelines for implementing regulations, and/or the like. For instance, the regulatory information may include information relating to regulations issued by the Departments of Health and Human Services, Labor, and Treasury that require insurance plans/issuers to cover certain preventive services delivered by in-network providers without any cost-sharing. And such information may include information relating to the preventive care recommendations propagated by the US Preventive Services Task Force (Task Force).

The interface(s) 115(a) . . . (n) may include for example without limitation a web interface allowing for transfer of and access to one or more of biographical information, demographical information, medical information, medical conditions, care provided, preventive care recommendation information, preventative care eligibility, payer coverage, regulatory information, etc. The personal data sources 114(a) and other data source(s) 114(n) may have web site/portals giving access to such information. As addressed previously, the personal data sources 114(a) may correspond to health management platforms/services that may be linked to the health information handling system 106 via the network 104 so that patient-related information retained by the personal data sources 114(a) may be accessed by/transferred to the health information handling system 106. The interface(s) 115 (a) . . . (n) may include any suitable input/output module or other system/device operable to serve as an interface between the personal data sources 114(a) and other data source(s) 114(n) and the network 104. The interfaces 115(a) . . . (n) may facilitate communication over the network 104 using any suitable transmission protocol and/or standard. In some embodiments, the health information handling system 106 may include and/or provide one or more of the interfaces 115(a) . . . (n), for example, by making available one or more of a website, a web page, a web portal, a web application, a mobile application, enterprise software, and/or any suitable application software.

One or more of the healthcare provider(s) 102, the healthcare payer(s) 112, the personal data source(s) 114(a), and/or the other data source(s) 114(n) may contain confidential health information for patients. Confidential health information may include, without limitation, any information on one or more of health conditions, medical conditions, characterizations, assessments, test results, and/or various metrics for specific patients, biographical/demographical information for specific patients, prescription information for specific patients, immunization records for specific patients, care services provided to specific patients, including preventive care services provided to specific patients, and/or eligibility of specific patients for preventive care services. The confidential health information may be under regulatory control. The Health Insurance Portability and Accountability Act of 1996 (HIPAA) set forth regulatory policies, procedures, and guidelines to control confidential health information. As part of the regulatory control, HIPAA provided for maintaining privacy and security of confidential health information, contemplating various offenses relating to health care with civil and criminal penalties for violations.

With respect to preventive care services, current law requires insurance plans to cover specific preventive services. Screening services apply to specific populations: services for adults; services for women; and services for children. For example, preventive services for adults may include but not be limited to one or more of: abdominal aortic aneurysm screening; alcohol misuse screening; blood pressure screening; cholesterol screening; colorectal cancer screening; depression screening; diabetes screening; HIV screening; immunizations (e.g., hepatitis A, hepatitis B, herpes zoster, human papillomavirus, influenza (flu shot), measles, mumps, rubella, meningococcal, pneumococcal, tetanus, diphtheria, pertussis, varicella, etc.); obesity screening; tobacco use screening; and/or syphilis screening. Preventive services for women, for example, may include but not be limited to one or more of: well woman visits; anemia screening; UTI screening; breast/ovarian cancer counseling for genetic testing; breast cancer mammography; breast cancer chemoprevention counseling; cervical cancer screening; folic acid supplements; gestational diabetes; gonorrhea screening; hepatitis B screening; HPV DNA testing; osteoporosis screening; and/or RH incompatibility screening. Preventive services for children, for example, may include but not be limited to one or more of: autism screening; blood pressure screening; cervical dysplasia screening; congenital hypothyroidism screening; depression screening; dyslipidemia screening; gonorrhea preventive medication; hearing screening; hematocrit/hemoglobin screening; sickle cell screening; HIV screening; immunization; obesity screening; oral health risk assessment; phenylketonuria screening; sexually transmitted infection screening; tuberculin testing; and/or vision screening.

The confidential health information may be in the form of an electronic medical record(s), which may include any health and/or medical record maintained in electronic form by a healthcare provider and/or healthcare payer. A HIPAA compliant electronic data format, 270/271, may be utilized for the purposes of making and receiving insurance eligibility and benefits information. However, this format is not considered limiting and other HIPAA or non-HIPAA compliant electronic data formats can be used and are considered within the scope of the present disclosure. In certain embodiments, the confidential health information may be in the form of a personal health record(s), which may include any electronic health medical record maintained by the patient that is typically stored on an internet-accessible database and/or website.

FIGS. 2A, 2B, and 2C depict one possible non-limiting example 200 of confidential health information that may be retained and/or available for a patient from a source. For instance, a healthcare payer 113, such as Medicare, may provide something akin to the example 200 to a patient via a web portal, responsive to the patient's request for the information. The healthcare payer 113 may provide similar information in delimited form, an XML format, and/or any suitable form.

In the example 200 depicted, information 202 corresponds to a personal profile for a particular patient. Personal profile information could include biographical information such as name, address, contact information, gender, date of birth, etc. Personal profile information could include other information such as height, weight, and blood type, for example. Information 204 corresponds generally to patient-reported information. The patient-reported information could include information on any one or combination of emergency contact details, medical conditions, allergies, implantable devices, family medical history, drugs, providers, pharmacies, immunization, lab tests/results, and/or vital statistics. Such items of information as that depicted in the example information sections 202, 204 may be consolidated by the system 106, checked against other information from other sources, and stored in one or more information repositories, a discussed further herein.

Information 206 corresponds to preventive services for which the patient is eligible as determined by a particular payer. In some cases, eligibility for a given service may be driven by reimbursement guidelines of multiple healthcare payers. Information 208 corresponds to healthcare plans and coverage relative to the patient. In general, example 200 may be based on information from one payer, much of which information may dependent on self-reporting of a patient, which may not be the most reliable source of information in some cases. Patients oftentimes move between healthcare payers, do not fully report all relevant health information, and do not have the wherewithal to deal with inconsistencies, inaccuracies, isolations, and other difficulties. Such items of information as that depicted in the example information section 206 may be checked against other information from other sources, consolidated by the system 106, and stored in one or more information repositories, as discussed further herein.

Referring again to FIG. 1, in various embodiments, the data from any one or combination of the healthcare providers 102, the healthcare payers 112, the personal data sources 114(a), and/or the other data sources 114(n) may be retrieved and/or received by the health information handling system 106 via the network 104 and/or through any other suitable means of transferring data. The data transferred to the health information handling system 106 may include any suitable data related to healthcare. The health information handling system 106 may function in part as an aggregator of health information. In so doing, the consolidation of health information from various data islands may accord a measure of reliability, consistency, comprehensiveness, thoroughness, and/or accuracy to the data gathered.

According to certain embodiments, data may be actively gathered and/or pulled from any one or combination of healthcare providers 102, the healthcare payers 112, the personal data sources 114(a), and/or the other data sources 114(n)—for non-limiting example, by accessing a repository that corresponds to those entities/individuals. Data could be gathered by "crawling" the various repositories in some embodiments. In addition or in the alternative, data may be pushed from any one or combination of healthcare providers 102, the healthcare payers 112, the personal data sources 114(a), and/or the other data sources 114(n) to the health information handling system 106. Updates for repositories may be periodically found. With some embodiments, any one or combination of healthcare providers 102, the healthcare payers 112, the personal data sources 114(a), and/or the other data sources 114(n) may provide notice to the health information handling system 106 of data to be transferred, such as updated information not previously pulled/pushed to the health information handling system 106. With some embodiments, data may be updated at the health information handling system 106 after a user logs into/initiates the website, a web page, a web portal, a web application, a mobile application, enterprise software, and/or any suitable application software. With some embodiments, data may be updated after a user specifies a particular patient and is authenticated as a user. Data pulled and/or pushed may be processed by the health information handling system 106 in accordance with certain embodiments described herein. Certain embodiments may also include data being pre-loaded and/or directly transferred to the health information handling system 106 (e.g., via a storage medium) in addition to or in lieu of transferring data via the network 104.

Figure 3:
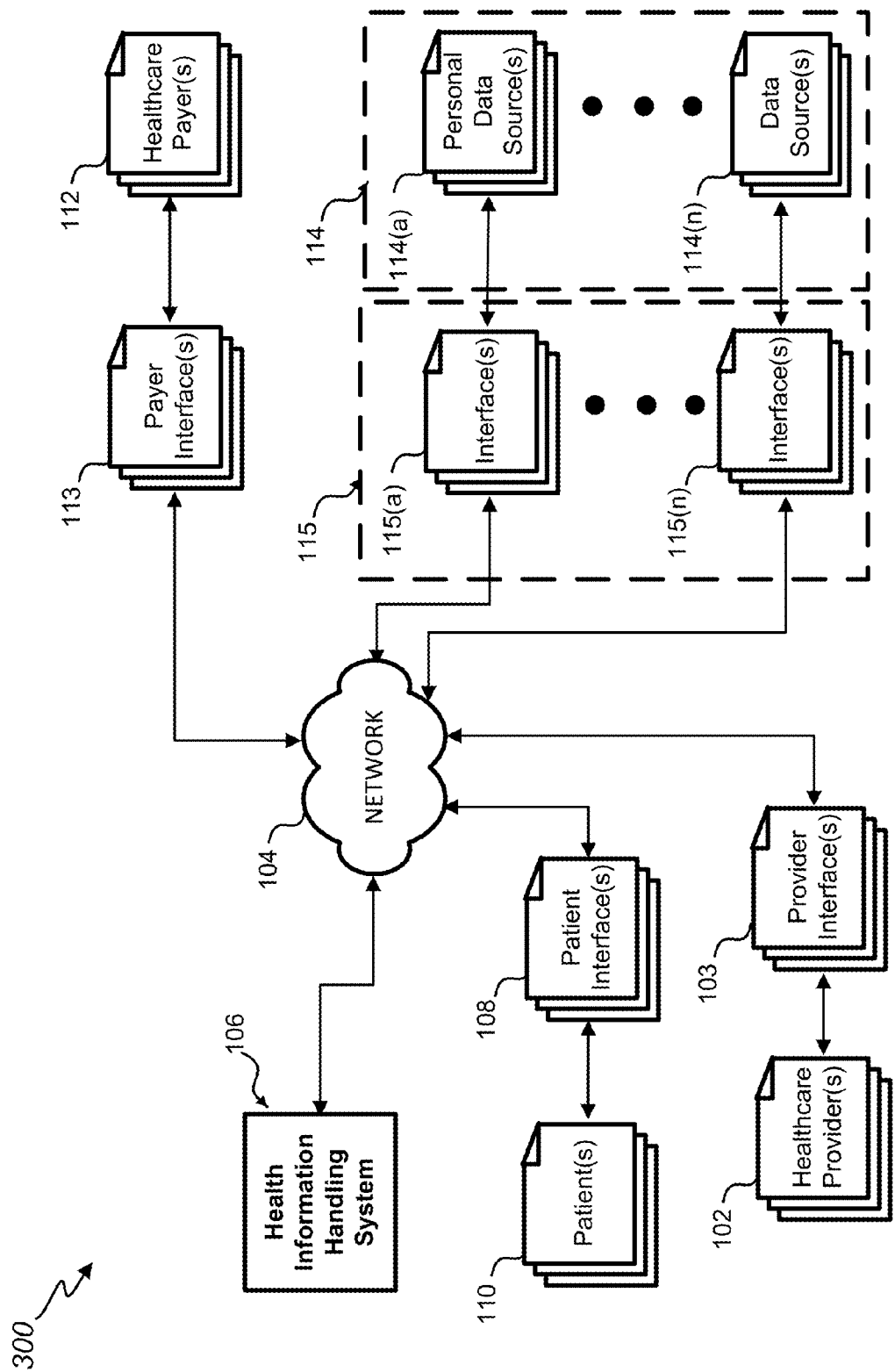
FIG. 3 depicts a high-level block diagram of a system, in accordance with certain embodiments of the present disclosure.

FIG. 3 depicts a high-level block diagram of a system 300, in accordance with certain embodiments of the present disclosure. The system 300 may be the same as or substantially similar to the system 100, except that the system 300 may allow for access by one or more patients 110. The patient 110, or legal representatives thereof, may access the health information handling system 106 through one or more patient interface(s) 108. As depicted, the one or more interfaces 108 may be communicatively coupled or couplable to the network 104. By way of example without limitation, an interface 108 may include a web portal accessible from network 104, and the health information handling system 106 may include, provide, and/or facilitate an application to the patient 110. In certain embodiments, the health information handling system 106 may include and/or provide the patient interface 108, for example, by making available one or more of a website, a web page, a web portal, a web application, a mobile application, enterprise software, and/or any suitable application software.

The patient interface(s) 108 may include for example without limitation a web interface allowing for transfer of and access to one or more of biographical information, demographical information, medical information, medical conditions, care provided, preventive care recommendation information, preventative care eligibility, payer coverage, regulatory information, etc. Certain embodiments may provide a web-based health management service for the patient 110. With some embodiments, the patient 110 may access the patient's aggregated health information serviced by the health information handling system 106. First time users, or legal representatives, might have to set up an account, along with authentication information. Consequent to authentication, a patient 110, or a legal representative, may have access to confidential health information for the patient 110, as discussed further herein.

Certain embodiments allow the patient 110 to track the patient's health information, consolidated from various sources into one place, via the patient interface 108. The patient 110 may be able to see what preventive services are recommended for the patient 110, see what preventive services are eligible for coverage by a healthcare payer and see the extent of coverage from zero cost-sharing to cost-sharing to no coverage. The patient 110 may be able to see what preventive services may be applicable but contingent upon further information to be provided by the patient 110 and/or the medical judgment of the patient's physician. The patient 110 may be given explanation(s), such as a Wiki or other explanation describing preventive services, applicability of preventive services, eligibility for coverage, what to expect with a preventive service, the importance of the preventive service, further information needed, other potentially relevant information, etc. Any one or combination of the foregoing may be provided to the patient 110 through a single patient interface 110. In some embodiments, the patient 110 could provide additional self-reported information. Having the ability to review the aggregated information pertinent to the patient 110, the patient 110 could correct certain information or otherwise indicate a need for correction.

Figure 4:
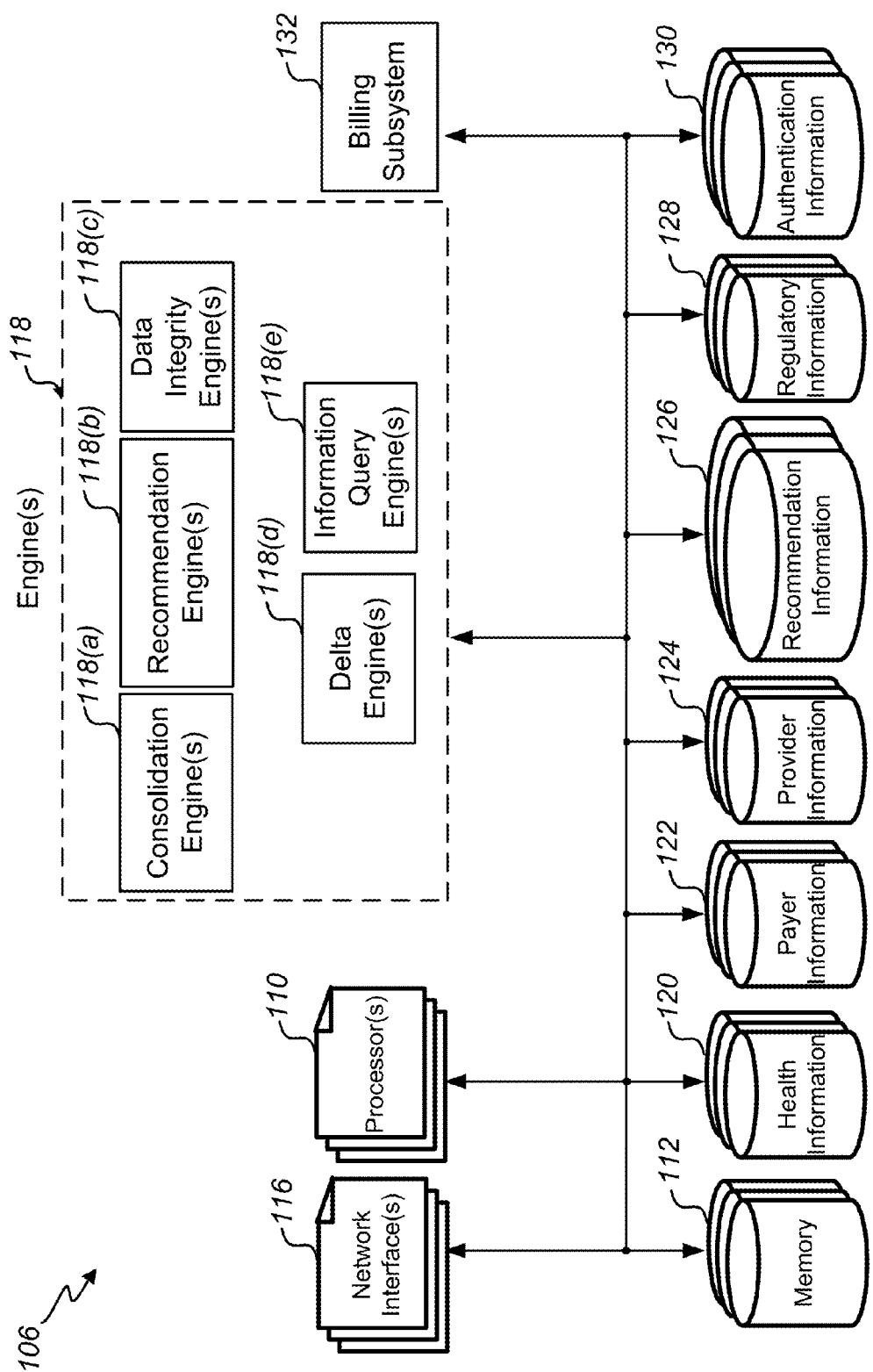
FIG. 4 depicts a high-level block diagram of a system, in accordance with certain embodiments of the present disclosure.

FIG. 4 shows a high-level block diagram of one embodiment of the health information handling system 106, in accordance with certain embodiments of the present disclosure. As depicted in FIG. 4, the health information handling system 106 may include one or more processors 110 communicatively coupled to one or more memories 112. The health information handling system 106 may be implemented in or with a distributed computing and/or cloud computing environment with a plurality of servers and cloud-implemented processing, memory, and data resources. Thus, with accretion of health information, the system may allow for scaling out with additional processing resources, server resources, data storage resources, data management resources, and the like.

The health information handling system 106 may include one or more network interfaces 116 communicatively coupled to processors 110. The network interface(s) 116 may include any suitable input/output module or other system/device operable to serve as an interface between one or more components of the health information handling system 106 and the network 104. The health information handling system 106 may use the network interfaces 116 to communicate over the network 104 using any suitable transmission protocol and/or standard.

One or more health information repositories 120 may retain any health information suitable for embodiments of this disclosure. The health information repositories 120 may include database(s), database management system(s), server(s) to facilitate management/provision/transfer of health information, and the like. The repositories 120 may retain confidential health information of particular patients. That confidential health information may include, without limitation, any information on one or more of health conditions, medical conditions, characterizations, assessments, test results, and/or various metrics for specific patients, biographical/demographical information for specific patients, prescription information for specific patients, immunization records for specific patients, care services provided to specific patients, including preventive care services provided to specific patients, and/or eligibility of specific patients for preventive care services. As discussed previously, the confidential health information may be aggregated from any one or combination of the healthcare providers 102, the healthcare payers 112, the personal data sources 114(a), and/or the other data sources 114(n).

One or more payer information repositories 122 may retain any suitable information related to healthcare payers. The payer information may include without limitation payer identification information, payer policy information, coverage/benefits guidelines/rules for services such as preventive care service, healthcare plans, explanations of benefits, in-network/preferred provider information, and the like. The payer information could indicate qualifying information necessary for determinations of coverage eligibility regarding certain preventive services. The payer information could include one or more of the foregoing items with respect to particular patients.

One or more provider information repositories 124 may retain any suitable information related to healthcare providers. The provider information may include without limitation provider identification information, provider location, amenities offered by providers, provider schedule information, technology offered by providers, preventive care service offerings information, in-network/preferred provider information, advertising information, provider billing information, reviews of providers, provider feedback, and the like. The provider information could, for example, be used to present preventive care service offerings/advertisements to a patient using the system.

One or more recommendation information repositories 126 may retain any suitable information related to preventive care recommendations. The recommendation information may include without limitation information relating the Task Force preventive care recommendations for primary care clinicians and health care systems such as information correlating preventive care recommendations and letter grades assigned by the Task Force, information relating to other preventive care recommendations from any source, and the like. The preventive care recommendations may be organized for correlation to confidential health information of particular patients. The recommendation information may include patient criteria/thresholds, such as gender, age, conditions, etc., for filtering to identify pertinent preventive care services for particular patients. The recommendations may be categorized according to whether they may be calendar-based or require some medical judgment. For fairly mechanical qualifications, timing information, such as thresholds of time for particular tests/therapies that indicate when the tests/therapies are applicable to patients, may be organized for ready correlation and identification of information required. For recommendations depending on medical judgment of a healthcare provider tending to a patient, information required/relevant may be likewise identified. In certain circumstances, previously prepared workflows may be specified for provider as guidance for preventive care service determinations. A workflow could include a decision tree to gather information used in diagnosis with areas of medical judgment left to the provider. The recommendation information may include information for Wikis or other explanations regarding preventive care services, why the recommendations are important, underlying studies, and the like. The recommendation information may include text, audio, video, and other rich media explanations.

One or more regulation information repositories 128 may retain any suitable information related to regulation of health information and preventive care. The regulation information may specify the regulatory rules for controlling health information from healthcare entities and patients. The regulation information may include without limitation regulations issued by a government authority, rules/guidelines for implementing regulations, and/or the like. For instance, the regulatory information may include information relating to regulations issued by the Departments of Health and Human Services, Labor, and Treasury that require insurance plans/issuers to cover certain preventive services delivered by in-network providers without any cost-sharing. The regulation information may include information relating to HIPAA regulatory policies, procedures, and guidelines for controlling and maintaining privacy/security of confidential health information.

One or more authentication information repositories 130 may retain any suitable authentication information to facilitate privacy and security for the system. The authentication information may include information to check credentials of a patient, a legal representative, a healthcare provider, and/or a healthcare payer that may use one of their corresponding interfaces to seek access to a patient's confidential health information and/or other system-provided features. The authentication information may be used to restrict the access granted to a certain set of information. For example, access may be restricted to information pertaining to an identified patient; and access may be further restricted to a subset of such information, as appropriate.

Any one or combination of the health information repositories 120, the payer information repositories 122, the provider information repositories 124, the recommendation information repositories 126, the regulation information repositories 128, and/or the authentication information repositories 130 may include database(s), database management system(s), server(s) to facilitate management/provision/transfer of health information, and the like. It should be appreciated that information corresponding to the repositories may be stored elsewhere and/or in other ways, or may not be stored, depending on the implementations chosen. Likewise, while various segregations of information corresponding to the repositories are provided herein, it should be appreciated that such examples are non-limiting, and some or all the information may be handled in any suitable manner.

The health information handling system 106 may include a billing subsystem 132. The billing subsystem 132 may handle billing aspects of accounting for the costs of preventive care services. The billing subsystem 132 may account for cost-sharing of services rendered or recommended. In some instances, multiple payers may be involved in covering a single preventive care service. The billing subsystem 132 may facilitate/coordinate the cost-sharing in such situations. Certain services are mandated by law to be covered by insurers/plans in whole or in part. The billing subsystem 132 may take such considerations into account. With payers, providers, and/or patients as users, breakdowns of coverage and cost-sharing may be provided.

Various embodiments of the health information handling system 106 may also include one or more engines 118 to implement any combination of features of embodiments described in the present disclosure. In various embodiments, the engines 118 may include one or more of consolidation engine(s) 118(a), recommendation engine(s) 118(b), data integrity engine(s) 118(c), delta engine(s) 118(d), and/or information query engine(s) 118(e). While the engines 118(a)-(e) are shown separately, it should be appreciated that in various embodiments the one or more engines 118 may be a consolidation engine, a recommendation engine, a data integrity engine, a delta engine, and/or an information query engine, collectively and/or integrally. The engines 118 may be stored in memory 112 and may include one or more software applications, executable with the one or more processors 110, for receiving and processing data requests. The engines 118 may be configured to perform any of the steps of methods described in the present disclosure.

By way of example without limitation, the consolidation engine(s) 118(a), with one or more the processors 110, may utilize one or more network interfaces 116 to access one or more of the healthcare provider(s) 102, the healthcare payer(s) 112, the personal data source(s) 114(a), and/or the other data source(s) 114(n) through the network 104. The health information handling system 106 may pull and/or push confidential health information from those entities in any suitable way. The consolidation engine 118(a) could process data pulled and/or pushed from the entity. In some instance, health information could be pre-loaded and/or directly transferred to the health information handling system 106 (e.g., via a storage medium) in addition to or in lieu of transferring data via the network 104. The consolidated data may be retained in one or more of the aforementioned repositories.

The consolidation engine 118(a) may accord a measure of reliability, consistency, comprehensiveness, thoroughness, and/or accuracy to the confidential health information that corresponds to a specific patient. All of the specific patient's health information may be consolidated into one place. The consolidation engine 118(a) may access manifold sets of confidential health information that corresponds to a specific patient. For instance, different sets of information may come from different sources. Different sets of information could come from the same source, for example, by way of one or more updates to information previously provided by a particular source for a particular patient. The sets could include, for non-limiting example, indications of a health condition of a particular patient and a health care service that has been provided to the patient. The consolidation engine 118(a) may consolidate the sets of confidential health information for the particular patient. Having determined the sets correspond to an identified patient, the consolidation engine 118(a) may form a composite set of confidential health information. The consolidation may include organizing, categorizing, qualifying, and/or comparing the sets of information; detecting, identifying, and/or handling errors/discrepancies; and/or otherwise processing the sets of confidential health information for the identified patient. Thus, the health information may be automatically organized into easy-to-understand categories. The consolidation engine 118(a) may store the composite set of confidential health information for the identified patient. For example, the composite set of information may be retained in one or more of the health information repositories 120.

The consolidation engine 118(a) may acquire and store authentication information in the one or more authentication repositories 130. The authentication information may be for a user that is approved for access to at least part of the composite set of confidential health information for the identified patient. For example, the user, who may be the patient, a legal representative, or a healthcare provider, may use one of the interfaces 103, 108 to seek access to the patient's confidential health information. The user may provide a set of credentials in order to gain access. The authentication information, which may be of any suitable form and content, may be retrieved and used to check the credentials provided. Pursuant to authentication, the user may have access to some or all of the composite set of information corresponding to the identified patient. The access could be limited to any suitable confines to maintain privacy.

With certain embodiments, the recommendation engine(s) 118(*b*), with one or more processor(s) 110, may be configured to provide a preventative care recommendation corresponding to a patient. The recommendation engine 118(*b*) may identify a patient. In some embodiments, the identification of the patient may be initiated by a healthcare provider; in some embodiments, the identification of the patient may be initiated by another user such as the patient. The recommendation engine 118(*b*) may derive confidential health information for the identified patient from a source, for non-limiting example, by pulling and/or pushing confidential health information one or more of the healthcare providers 102, the healthcare payers 112, the personal data sources 114(*a*), and/or the other data sources 114(*n*)—or by processing pre-loaded and/or otherwise directly transferred confidential health information. The recommendation engine 118(*b*) may access confidential health information—for non-limiting example, confidential health information stored in one or more health information repositories 120.

The recommendation engine 118(*b*) may access one or more sources to identify a set of criteria indicating a preventative care service. In so doing, the recommendation engine 118(*b*) may access one or a combination of the health information repositories 120, the payer information repositories 122, the provider information repositories 124, the recommendation information repositories 126, the regulation information repositories 128, and/or the authentication information repositories 130. Accordingly, in various embodiments, the set of criteria may be based on various items of information.

By way example without limitation, in certain embodiments, the criteria may be based in part on that which may be stored in the payer information repositories 122. Thus, criteria could correspond to requirements for payer coverage of one or more preventive care services, and may indicate whether one or more preventive care services are eligible for payment by the payer. In certain embodiments, the criteria may be based at least partially on that which may be stored in the provider information repositories 124. Thus, criteria could be based in part on provider location, amenities offered by providers, provider schedule information, technology offered by providers, preventive care service offerings information, and/or in-network/preferred provider information, etc. In certain embodiments, the criteria may be based at least partially on that which may be stored in the recommendation information repositories 126. Thus, criteria could be based in part on preventive care recommendations information (e.g., derived from the Task Force) that may include patient criteria/thresholds, such as gender, age, conditions, etc., for filtering to identify pertinent preventive care services for particular patients. In certain embodiments, the criteria may be based at least partially on that which may be stored in the regulation information repositories 128. Thus, criteria could be based in part on regulations issued by a government authority, rules/guidelines for implementing regulations, and/or the like. In certain embodiments, the criteria may be based at least partially on that which may be stored in the authentication information repositories 130. Thus, criteria could be based in part on restrictions of access may to information pertaining.

The recommendation engine 118(*b*) may take into account the set of criteria, and may generate a specific recommendation corresponding to the identified patient. The recommendation may be tailored for a healthcare provider of the patient in some embodiments. In some embodiments, the recommendation may be tailored for the patient. The recommendation engine 118(*b*) may correlate confidential health information of the patient to the set of criteria in view of one or more preventive care recommendations. Items of confidential health information of the patient may be compared to details of the preventive care recommendations to determine which recommendations are applicable to the patient (e.g., calendar-based recommendations) and which recommendations may be applicable to the patient depending on medical judgment of a healthcare provider tending to the patient and/or depending on additional information that is needed to make the determination. Recommendations with A and B may entail fairly mechanical qualifications such as when the last time the particular test or therapy was performed (i.e., calendar-based recommendations).

The payer may have reimbursement guidelines that might specify what qualifying information needed in order to determine services for which the payer will provide payment. Where additional information is required in certain circumstances, a workflow can be specified for a healthcare provider that could include a decision tree to gather information used in diagnosis with areas of medical judgment left to the provider. Any answered questions may be fed back to the recommendation engine 118(*b*). The preventative care guidelines may be provided along with the information needed to comply with reimbursement eligibility. Different payers can have different preventative care guidelines along with reimbursement eligibility such that each patient might have a customized interaction with the provider.

With certain embodiments, the data integrity engine(s) 118 (*c*), with one or more processor(s) 110, may check health information to ensure quality of data underlying particular preventative care recommendations for a particular patient. The data integrity engine 118(*c*) may assess each piece of information underlying a recommendation and may assign a weight to the information according to a score. Any suitable scoring system may be used. Missing information, for example, could have a lower score than non-missing information; and the missing information could be scored even lower, the more important the information is to the recommendation. Information may be weighted according to the source. For example, in some instances, information gathered from a healthcare provider may be weighted higher or lower relative to information gathered from a patient; test results gathered from a healthcare provider, for example, may be considered more reliable than corresponding/conflicting information self-reported by the patient. Scoring recommendations based the information based upon the underlying reliability of information may avoid redundant, potentially harmful and/or unnecessary preventive care. The data integrity engine 118(*c*) may utilize one or more network interfaces 116 to convey the results of the recommendation scoring to a user.

In certain embodiments, the data integrity engine 118(*c*) may examine items of information and assign scores according to how important such information is to prevent care service recommendations, generally. In certain embodiments, the data integrity engine 118(*c*) may adjust scoring of information in view of a specific prevent care service recommendation(s). In certain embodiments, the data integrity engine 118(c) may examine items of information in view of a specific prevent care service recommendation(s) upfront, thereby rendering subsequent readjustment unnecessary.

Based on the scoring, possible follow-up questions and/or prompting for further information and/or clarifying information may be identified, generated, and/or provided. Accordingly, recommendations can be made more reliably with the provider asking possible follow-up questions and/or prompting for an account to link to for more missing health information. The data integrity engine 118(c) may utilize the network interface(s) 116 to convey the results of the recommendation scoring to a user.

The data integrity engine 118(c) may take into account preventive care recommendation categories. Data regarding the preventive care recommendations and categories may be prepared for correlating to the confidential health information of the patient. Certain categories may be eliminated as not being applicable to the patient. For example, prevent care recommendations specific to women could be eliminated for a male patient, prevent care recommendations specific to pregnant women could be eliminated for a non-pregnant female patient, etc. Certain categories may be identified as of particular relevance to the patient, for example, based on a history of the patient retained by the system.

With certain embodiments, the delta engine(s) 118(d), with one or more processor(s) 110, may be configured to handle changes in preventive care recommendations. The preventative care delta engine 118(d) may recognize changes in the preventive care guidelines (e.g., those issued by the Task Force and/or implemented by law/regulation). The health information handling system 106 may be linked to a site that provides updates on such changes, may periodical crawl for updates and changes, and/or may otherwise receive notice of changes in the guidelines. The delta engine 118(d) may process the changes to identify exactly what has changed, the scope of the changes, and the potential ramifications. The delta engine 118(d) may prepare data, regarding details, scope, extent, and/or potential ramifications of the changes, for correlating to the confidential health information of particular patients. For non-limiting example, it may be determined that the changes affect certain preventive services, certain types of patients, certain payers, etc.; it may also be determined that the changes translate to greater or lesser thresholds for preventive care service applicability to certain patients and/or eligibility for cost-sharing by payers.

The delta engine 118(d) may identify patients potentially affected by the changes. The identification of the patient may be based on the determinations that the changes affect certain preventive services, certain types of patients, certain payers, etc., and correlating those determinations with the patient. The delta engine 118(d) may compare the data regarding the changes to confidential health information of the identified patient. Past recommendations and treatments/tests/therapies may be considered in order to correct any out-of-date information or recommendations. In so doing, the delta engine 118(d) may determine the effects of the changes in preventive care recommendations on the identified patient. Then, the delta engine 118(d) may notify providers and/or patients of those changes. The delta engine 118(d) may be a check for a preferred method of contact stored in the information handling system for the provider and/or patient. Any suitable means of notification may be employed. For example, text, voice, e-mail, and/or paper mail notifications could be sent to those affected by the revisions. The notification could include a link or other communication reference referring back to a provider/payer site and/or health information portal provided by the health information handling system 106 to get the confidential information about the effects of the changes in the preventive care recommendations on the identified patient. The provider and/or patient also could be sent reminders to see their primary care provider or a provider of the recommended preventive care. The reminders could be periodically sent according to the provider and/or patient preferences stored in the health information handling system 106.

With certain embodiments, the information query engine(s) 118(e), with one or more processor(s) 110, may be configured to handle searching of one or more information repositories. Other engines 118 may include and/or utilize the information query engine 118(e) in various embodiments. The searching may be in response to information received over the network 104 from a user. The information query engine 118(e) may allow for user identification of various suitable search criteria, according to various embodiments. By way of example without limitation, the information engine 118(e) may receive a query from a provider, payer, or patient, where the query is transferred over the network 104 to the health information handling system 106. In certain embodiments, the query may have a packetized structure according to a packet protocol, and may include one or more search terms. Responsive to the query, the information query engine 118(e) may search, retrieve, modify, and/or cause transfer of particular information from one or more information repositories.

Figure 5:
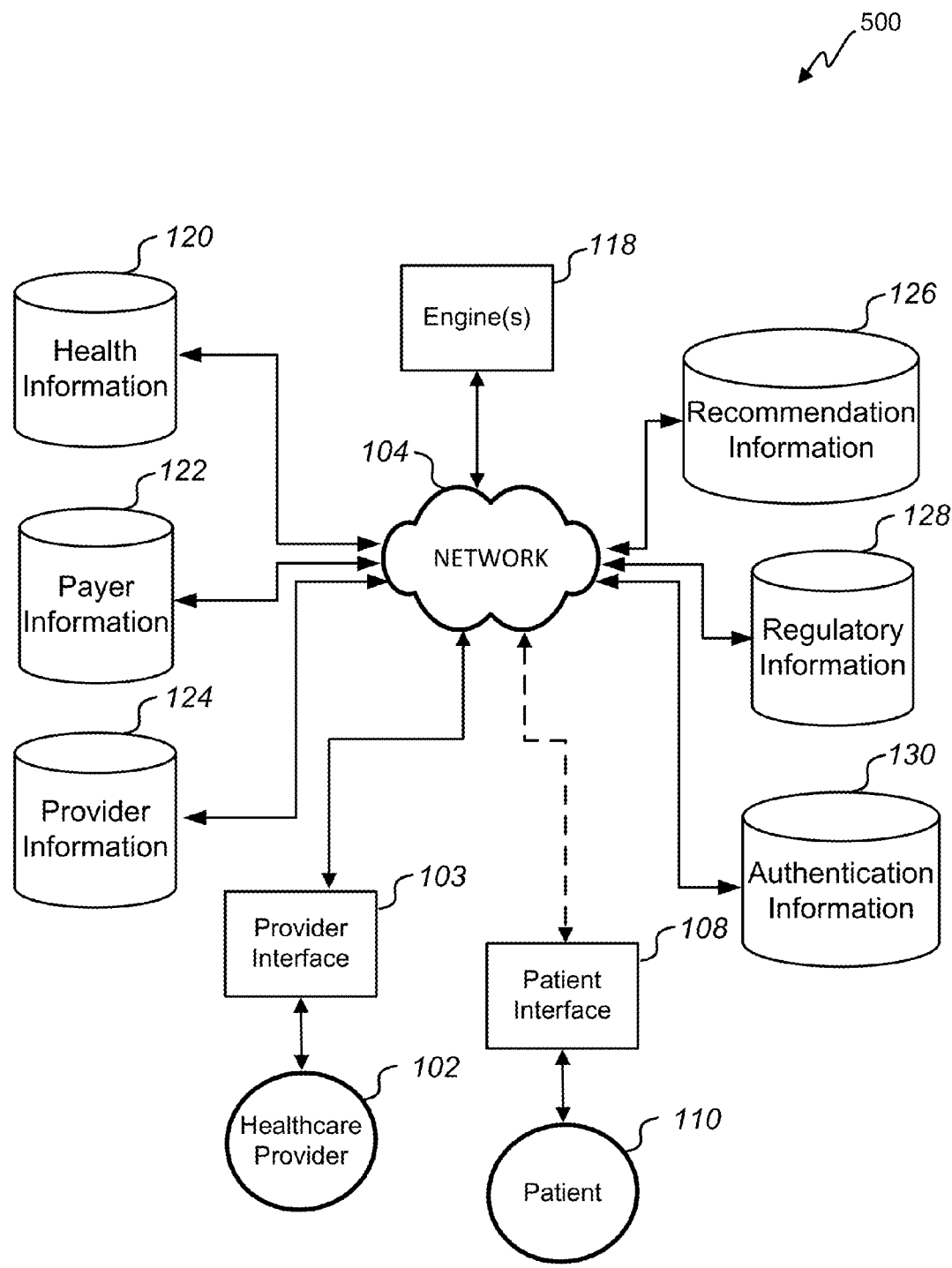
FIG. 5 depicts a high-level block diagram of a system, in accordance with certain embodiments of the present disclosure.

FIG. 5 is a block diagram of a system 500, in accordance with certain embodiments of the present disclosure. The system 500 may correspond to systems previously discussed but may focus on some possible interaction of the healthcare provider 102 and/or the patient 110 in some embodiments. The healthcare provider 102 or the patient 110 may log into the system 500 as a user via the provider interface 103 or patient interface 108, respectively. As noted previously, the interfaces 103, 108 may each include a mobile computing device or any other computing device. With some embodiments, one or both the interfaces 103, 108 may include a mobile application installed on a mobile computing device for the provider/patient to use. The mobile application may be available for download, for non-limiting example, from the health information handling system 106. With some embodiments, one or both the interfaces 103, 108 may include a web page, a web portal, a web application, enterprise software, and/or any suitable application software for the provider/patient to use.

In the case of the healthcare provider 102 or patient 110 having previously set up an account, the user's credentials provided with login may be authenticated according to authentication information previously stored in the authentication information repository 130. Responsive to a login attempt, the authentication information repository 130, which could correspond to one or more servers, dedicated or shared, in some embodiments, may for example facilitate access to authentication information previously stored for the particular patient. The engine(s) 118 could facilitate authentication in conjunction with the authentication information repository 130.

Consequent to authentication, the user may have access to certain confidential health information. In the case of the healthcare provider 102, the accessible confidential health information may be relegated to a set of one or more patients previously identified as under the provider's care, identified as part of the authentication, or subsequently identified by the provider. The healthcare provider 102 could be allowed to select a particular patient from a list of patients or input an identifier for the particular patient. In the case of the patient 110, the accessible confidential health information may be relegated to only the patient's information.

Consequent to identification of the particular patient, the interface 103 may present the patient's information. The patient's information could be arranged in any suitable way. For example, the patient's information could be arranged in the manner of a dashboard such that the provider may have a global view of the patient's information and/or categories of patient information. The health information may have been consolidated by the engines 118 from various sources and automatically categorized into easy-to-understand categories. Items of information for selection by the provider may include without limitation biographical information, demographical information, medical information, medical conditions, care provided, preventive care recommendation information, preventative care eligibility, payer coverage, regulatory information, etc. Dashboard items corresponding to such information may be categorized in any appropriate manner for ease of access and efficacy of presentation. The provider could be able to select and view a report of certain health information of the patient. For instance, the user could view the patient's medical conditions information retained in the system. Responsive to user selection, the health information repository 120, which in some embodiments could correspond to one or more dedicated or shared servers, may for example facilitate access to aggregated health information for the particular patient. The engine(s) 118 could facilitate access to the health information in conjunction with the health information repository 120.

The user may be provided an option for the to view certain payer information corresponding to the particular patient. The payer information repository 122, which could correspond to one or more servers, dedicated or shared, in some embodiments, may for example facilitate access to aggregated payer information for the particular patient. The provider may wish to view the provider information and select that option. Responsive to user selection, the provider information repository 124, which could correspond to one or more servers, dedicated or shared, in some embodiments, may for example facilitate access to aggregated provider information for the particular patient. The engine(s) 118 may facilitate access to the health information in conjunction with the health information repository 120.

The interface 103 may provide an option for the user to view payer information. Responsive to user selection, the interface 103 may provide payer information including without limitation payer identification information, payer policy information, coverage/benefits guidelines/rules for services such as preventive care service, healthcare plans, explanations of benefits, in-network/preferred provider information, and the like, in general and/or with respect to the particular patient. The payer information could indicate qualifying information necessary for determinations of coverage eligibility regarding certain preventive services. Responsive to user selection, the payer information repository 122, which in some embodiments could correspond to one or more dedicated or shared servers, may for example facilitate access to aggregated provider information for the particular patient. The engine(s) 118 may facilitate access to the health information in conjunction with the payer information repository 122.

The interface 103 may provide an option for the user to view certain preventive care services which are applicable to the patient and which are eligible for cost-sharing by a healthcare payer. By way of example without limitation, responsive to user selection, the interface 103 may present: preventive services recommended for a particular patient; preventive services eligible for coverage by a healthcare payer; and/or the extent of coverage from zero cost-sharing to cost-sharing to no coverage. Responsive to user selections, the recommendation information repository 126, which in some embodiments could correspond to one or more dedicated or shared servers, may for example facilitate access to recommendation information for the particular patient. The engine(s) 118 may facilitate access to the recommendation information in conjunction with the recommendation information repository 126.

With the patient having already been identified and the possible preventive care recommendations and categories having been taken into account, certain categories of services may have been already eliminated as not being applicable to the patient. For example, prevent care recommendations specific to men could be eliminated for a female patient, prevent care recommendations specific to pregnant women could be eliminated for a non-pregnant female patient, etc. Hence, the healthcare provider 102 need only see which preventive care services are relevant to the particular patient. Certain categories may be identified as of particular relevance to the patient, for example, based on a patient history previously retained.

In certain embodiments, the user may only see the results of correlation of the patient's health information to preventive care recommendations, such as those propagated by the Task Force. The interface 103 may present preventive care recommendations, indicating which recommendations are applicable to the patient (e.g., calendar-based recommendations) and recommendations which may be applicable to the patient depending on medical judgment of a healthcare provider tending to the patient and/or depending on additional information that is needed to make the determination. The interface 103 may present options for the user to identify criteria needed for applicability/eligibility, explanation(s), and/or other potentially relevant information. The interface 103 may present options for user to identify regulation information pertinent to the recommendations. The regulation information may be provided with the recommendation information repository 126, and may include, for example, regulations issued by a government authority, rules/guidelines for implementing regulations, and/or the like.

The interface 103 may provide options for explanations describing preventive services, applicability of preventive services, eligibility for coverage, reimbursement guidelines that might specify what qualifying information is needed in order to determine services for which the payer will provide payment, the importance of the preventive service, any other further information needed, other potentially relevant information, etc. The explanations may be directed to patient perspective or a provider, depending on whether the user is a patient or a provider. With some embodiments, the interface 103 may provide an option to view a workflow can be specified for the healthcare provider 102. The workflow could include a decision tree to gather information used in diagnosis with areas of medical judgment left to the provider. The workflow could include potential questions for provider's use. With some embodiments, The healthcare provider 102 may provide input via the interface 103. The input may include, for example, corrections to information presented, additional information obtained from examination of the patient, determinations made in the provider's medical judgment, etc. In some embodiments, the patient 110 may provide input via the interface 108, the input being similar but confined to appropriate content from a patient's perspective. Pursuant to the input being received, the interface 103 may present an option to regenerate preventive care recommendations, taking the provider's/patient's input into account.

Figure 6:
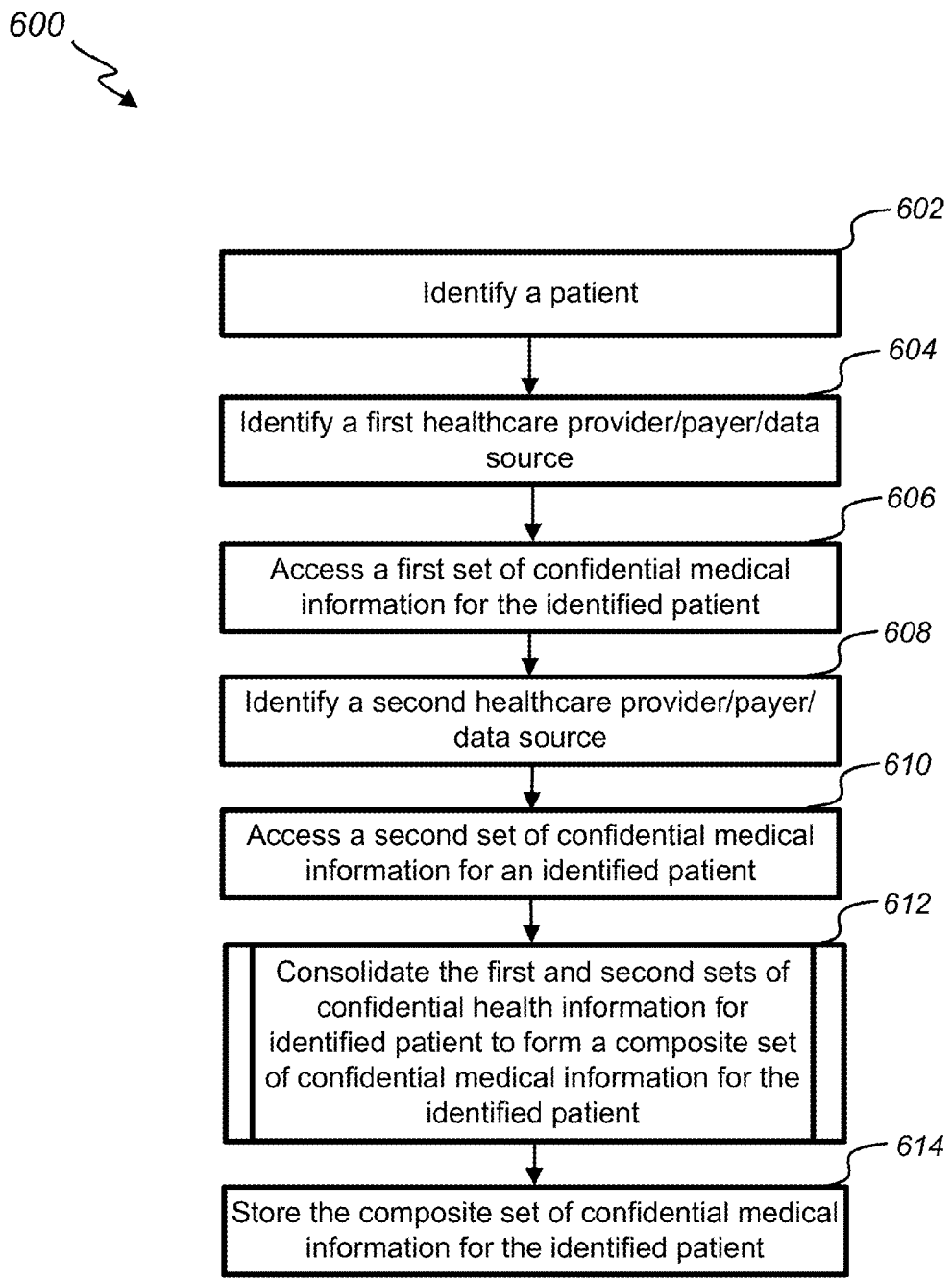
FIG. 6 illustrates an example method of consolidating health information under regulatory control from healthcare entities and patients, in accordance with certain embodiments of the present disclosure.

FIG. 6 illustrates an example method 600 of consolidating health information under regulatory control from healthcare entities and patients, in accordance with certain embodiments of the present disclosure. Teachings of the present disclosure may be implemented in a variety of configurations that may correspond to the systems disclosed herein. As such, certain steps of the method 600, and the other methods disclosed herein, may be omitted, and the order of the steps may be shuffled in any suitable manner and may depend on the implementation chosen. Moreover, while the following steps of the method 600, and those of the other methods disclosed herein, may be separated for the sake of description, it should be understood that certain steps may be performed simultaneously or substantially simultaneously.

According to one embodiment, the method 600 may begin at step 602. At step 602, a particular patient is identified. At step 604, a first data source is identified. The data source may correspond to one or more of a healthcare provider 102, a healthcare payer 112, a personal data source 114(a), another data source 114(n), a repository of one or more of those entities, and/or information corresponding thereto. Data may be actively gathered and/or pulled from one or more sources, for non-limiting example, by accessing a third party repository. Data could be gathered by "crawling" the various repositories in some embodiments. With some embodiments, sites of data sources may be linked with the health information handling system 106 so that updates available through the linked sites may be periodically found. In some embodiments, a web site/portal corresponding to a repository may be linked to the health information handling system 106 to facilitate notice and/or transfer of updated information. In addition or in the alternative, data may be pushed from one or more data sources to the health information handling system 106.

As indicated by step 606, a first set of confidential health information for the identified patient may be accessed. The information may have come from the first data source and may include indications of a health condition of a particular patient and a health care service that has been provided to a particular patient. The information may have been retained in a memory and/or repository before step 604; alternatively, the information may be retained in a memory and/or repository simultaneously with or consequent to step 604.

As indicated by step 608, a second data source is identified. Again, the second data source may correspond to one or more of a healthcare provider 102, a healthcare payer 112, a personal data source 114(a), another data source 114(n), a repository of one or more of those entities, and/or the information corresponding thereto. As indicated by step 610, a second set of confidential health information for the identified patient may be accessed. The second set may be different from the first. Different sets of information could be derived from the same data source, for example, by way of one or more updates to information previously provided by a particular data source for a particular patient. The sets could include, for non-limiting example, indications of a health condition of a particular patient and a health care service that has been provided to the patient. Different sets of information could be derived from different data sources.

As indicated by step 612, the first and second sets of confidential health information for identified patient may be consolidated to form a composite set of confidential health information for the identified patient. The consolidation may include organizing, categorizing, qualifying, and/or comparing the sets of information; detecting, identifying, and/or handling errors/discrepancies; and/or otherwise processing the sets of confidential health information for the identified patient. As indicated by step 614, the composite set of confidential health information for the identified patient may be stored. For example, the composite set of information may be retained in a memory and/or repository.

Figure 7:
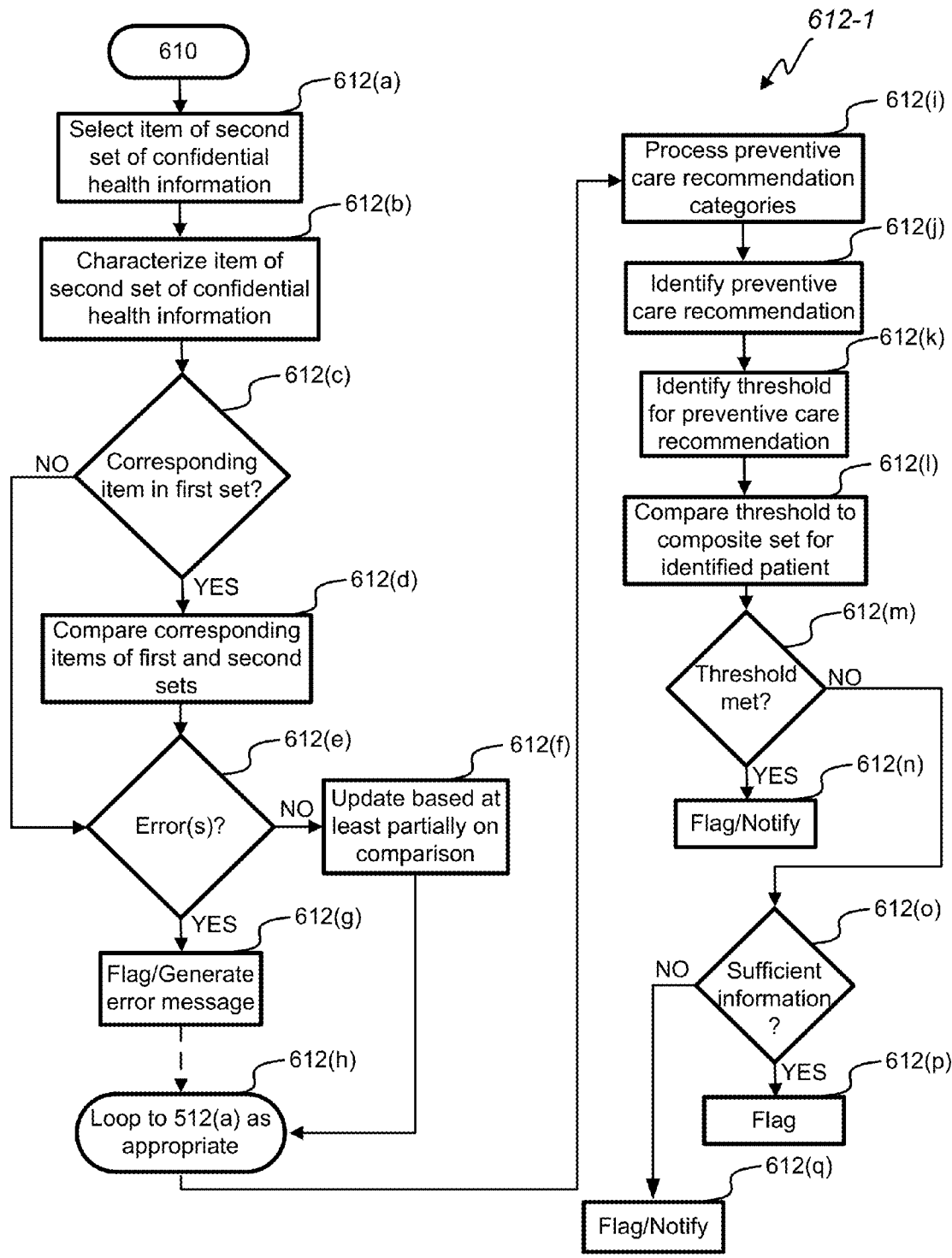
FIG. 7 illustrates an additional example subprocess corresponding to the method of FIG. 6, in accordance with certain embodiments of the present disclosure.

FIG. 7 illustrates an additional example subprocess 612-1 corresponding to step 612 of method 600, in accordance with certain embodiments of the present disclosure. One non-limiting example of the subprocess 612-1 may begin with a transition from step 610 to step 612(a). As indicated by step 612(a), an item of the second set of confidential health information may be selected. The item of second set of confidential health information may be characterized, as indicated by step 612(b). For non-limiting example, an item of information may be characterized/identified as one or more of belonging to a particular category of information (e.g., biographical information) and/or belonging to a particular sub-category of information (e.g., name of patient). Some embodiments may characterize the item of information further, for example, as coming from a particular source and being qualified accordingly (e.g., information may characterized as coming from a more or less reliable source), being more or less important than other items of information, and/or according to recency of information.

As indicated by step 612(c), it may be determined whether there is an item of information in the first set of confidential health information for the identified patient that corresponds to the selected and characterized item from the second set. The determination may be made based in part on the characterizations of the items. In the case of no corresponding item in the second set being identified, the item could be new information in a category for which no information had been previously received (e.g., the new information could indicate a blood type, whereas that could have been previously unknown to the health information handling system 106); and the flow may proceed to step 612(e). In the case of a corresponding item in the second set being identified, the items from the first and second may be compared, as indicated by step 612(d). As indicated by step 612(e), it may be determined if any errors are detected, in the form and/or content of the item(s) of information. In the case of no errors, the composite set of information may be formed/updated based at least partially on the comparison, as indicated by step 612(f). As indicated by step 612(g), if any errors are detected, the errors may be flagged. In certain embodiments, an error message may be generated. The process flow may loop back to the step 612(a) for processing of other items of information, as indicated by step 612(h).

After appropriate iteration with looping back through the previous steps, the process flow may transition to step 612(i), where preventive care recommendation categories may be processed. As discussed above, preventive care recommendations may be outlined according to a coding method, where a given recommendation is assigned a letter grade, such as A, B, C, etc. The recommendations can be calendar-based or require some medical judgment. Grade levels A and B, for example, may entail relatively mechanical qualifications, such as an amount of time since a particular test or therapy was last performed on a particular patient. The preventive care recommendation categories may be processed in view of the composite set of confidential health information for the identified patient. The recommendation categories may be filtered with patient criteria such as gender, age, conditions, etc. to identify pertinent preventive care services for the patient. One or more thresholds for preventive care services may be identified, as indicated by step 612(k). As one non-limiting example, a particular patient may be eligible for particular preventive care service once a year after age 65. As indicated by step 612(*l*), the threshold may be compared to the composite set of health information for the patient, and it may be determined at step 612(*m*) whether the threshold has been met. For non-limiting example, it may be determined if the patient is now due for an annual preventive care service which is eligible for coverage by the patient's healthcare payer. If the threshold is met, the condition may be flagged and/or the patient and/or healthcare provider/payer may be notified, as indicated by step 612(*n*). If the threshold is not met, it may be determined whether sufficient information is available in to the health information handling system 106 to make the threshold determination, as indicated by step 612 (*o*). If sufficient information is available, the condition may be flagged, as indicated by step 612(*p*). In such instances, the patient may simply not be eligible for the preventive care service for one or more reasons. For example, enough time may not have passed since the patient's last preventive care service for the patient to again be eligible for the next calendar-based recommended service. If sufficient information is not available, the information gap may be flagged, as indicated by step 612(*q*). In certain embodiments, the patient and/or healthcare provider/payer may be notified. Thus, where there are gaps in information, the gap instances are noted in order to prompt for getting that information. Preventative care recommendations needing information from those gaps in data are noted.

Figure 8:
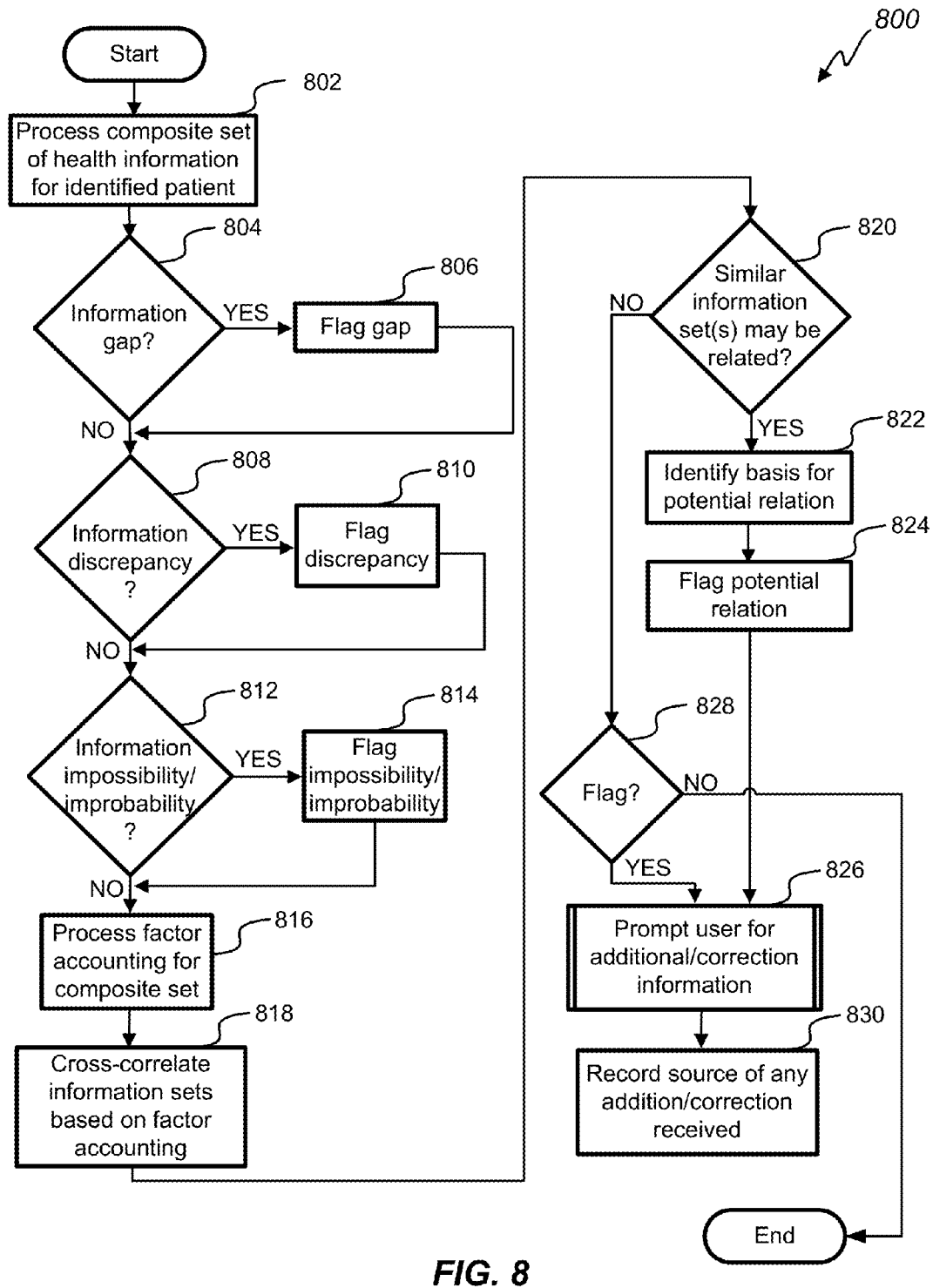
FIG. 8 illustrates a method for anomaly spotting by identifying gaps in information, conflicting information, impossible/improbable information, and/or similar records that may be related, in accordance with certain embodiments of the present disclosure.

FIG. 8 illustrates a method 800 for anomaly spotting by identifying gaps in information, conflicting information, impossible/improbable information, and/or similar records that may be related, in accordance with certain embodiments of the present disclosure. With some embodiments, aspects of method 800 may be performed with the health information handling system 106 and the data integrity engine 120. Certain data issues can be solved by linking together datasets that do not exactly match. Some embodiments include an algorithm that takes into account age, geography, address, and/or other factors that can be used to identify similar records that might be linked together. The source of any corrections and additions may be recorded for providence.

According to one embodiment, the method 800 may begin at step 802. At step 802, a composite set of confidential health information for an identified patient may be processed. For non-limiting example, the health information handling system 106 may access such information which may have been stored in a repository. As indicated by step 804, it may be determined whether one or more information gaps exist in the composite set. As one of many possible non-limiting examples, blood type information may be missing for the identified patient. Any gaps identified may be flagged, as indicated by step 806. As indicated by step 808, it may be determined whether one or more discrepancies exist in the composite set. As one of many possible non-limiting examples, there may be naming and identification issues, such as multiple spellings of a middle name of the identified patient. Any discrepancies identified may be flagged, as indicated by step 810. As indicated by step 812, it may be determined whether one or more impossibilities/improbabilities exist in the composite set. As one of many possible non-limiting examples, there may be a record of gender information that does not comport with a gender-specific service that was provided to the identified patient. Any impossibilities/improbabilities identified may be flagged, as indicated by step 814.

As indicated by step 816, factor accounting for the composite set may be processed. For non-limiting example, age, geography, address, and/or other factors of the composite set can be identified for use in identifying similar records that might be linked together with the composite set. As indicated by step 818, information set(s) may be cross-correlated based on the factor accounting. The factors could indicate a correlation between the composite set and one or more additional information sets. As indicated by step 820, it may be determined whether the information sets may be related. If so, the basis(es) for potential relation may be identified, as indicated by step 822, and the basis(es) and/or the potential relation, generally, may be flagged, as indicated by step 824. In the case of no similar information sets, at step 828, if there is no flagged condition per steps 806, 810, and/or 814, the process flow may end; if there is a flagged condition per steps 806, 810, and/or 814, the process flow may transition to step 826. As indicated by step 826, a user may be prompted for additional/correction information. If such information is received responsive to the prompting, the source of the information may be recorded for providence, as indicated by step 830.

Figure 9:
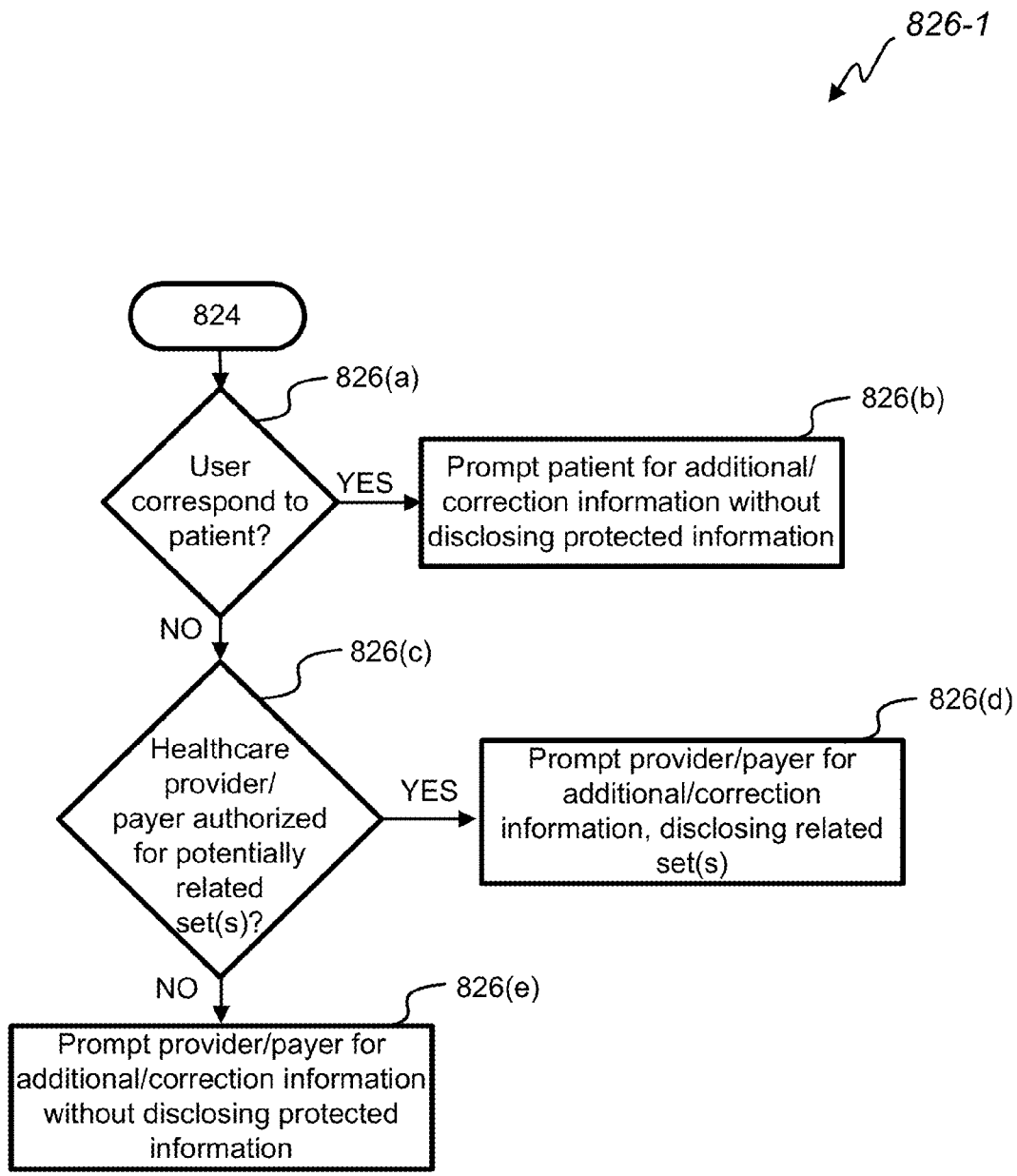
FIG. 9 illustrates an additional example subprocess corresponding to the method of FIG. 8, in accordance with certain embodiments of the present disclosure.

FIG. 9 illustrates an additional example subprocess 826-1 corresponding to step 826 of method 800, in accordance with certain embodiments of the present disclosure. Prompted by flagging, the provider, and, under some circumstances, the patient, can correct errors and/or add additional information. This may be done in a way that obscures HIPAA-protected and/or other protected information; and treatment of such information might be different as between the patient and provider, according to some embodiments.

One non-limiting example of the subprocess 826-1 may begin with a transition from step 824 to step 826(*a*). As indicated by step 826(*a*), it may be determined whether a user accessing the confidential health information corresponds to the identified patient or legal representative thereof. In the case of the user corresponding to the identified patient, the user may be prompted for additional/correction information, without disclosing protected information, as indicated by step 826(*b*). If the user does not correspond to the identified patient, the process flow may transition to step 826(*c*). It may be determined whether the user is a healthcare provider or payer that is authorized to access the composite set of the identified and the potentially related information set(s). If so, the healthcare provider/payer may be prompted for the additional/correction information, and the potentially related information set(s) may be disclosed to/provided for access by the healthcare provider/payer, as indicated by step 826(*d*). In the case of the healthcare provider or payer not being authorized to access the composite set of the identified and the potentially related information set(s), the user may be prompted for additional/correction information, without disclosing protected information, as indicated by step 826(*e*).

Figure 10:
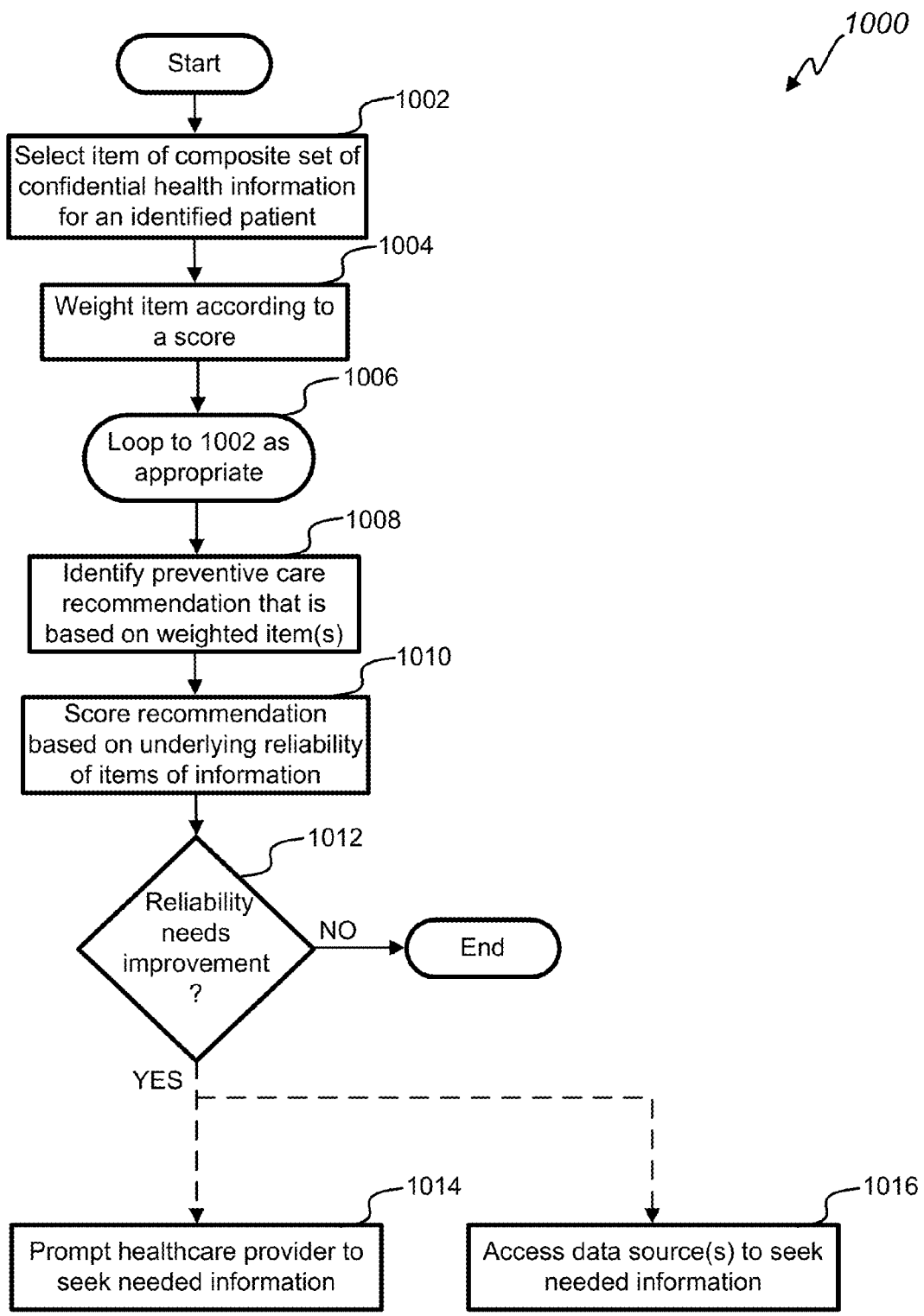
FIG. 10 illustrates a method for assessing/improving reliability of preventive care recommendations, in accordance with certain embodiments of the present disclosure.

FIG. 10 illustrates a method 1000 for assessing/improving reliability of preventive care recommendations, in accordance with certain embodiments of the present disclosure. With some embodiments, aspects of method 1000 may be performed with the health information handling system 106 and the data integrity engine 118(*c*). Preventative care recommendations can be affected by poor underlying data in the medical record. With some embodiments, each piece of information underlying a recommendation may be weighted according to a score. Missing information, for example, could have a lower score than non-missing information; and the missing information could be scored even lower, the more important the information is to the recommendation. Recommendations based the information may be scored based upon the underlying reliability to avoid redundant, potentially harmful and/or unnecessary preventive care. Recommendations can be made more reliably with the provider asking possible follow-up questions and/or prompting for an account to link to for more missing health information.

According to one embodiment, the method 1000 may begin at step 1002. As indicated by step 1002, item of the composite set of confidential health information for an identified patient may be selected. As indicated by step 1004, the item may be weighted according to a score. Missing information, for example, could have a lower score than non-missing information. Additionally, the missing information could be scored even lower, the more important the information is in recommendations, generally. In alternative or in combination, information may be weighted according to the source. For example, in some instances, information gathered from a healthcare provider may be weighted higher or lower relative to information gathered from a patient; test results gathered from a healthcare provider, for example, may be considered more reliable than corresponding/conflicting information self-reported by the patient.

As indicated by step 1006, the process flow may loop back to the step 1002 for processing of other items of information. After appropriate iteration with looping back through the previous steps, the process flow may transition to step 1008, where a preventive care recommendation categories based on the weighted item(s) may be identified. As indicated by step 1010, the recommendation may be scored based on an underlying reliability of the items of information. The scoring of the information items may be adjusted in view of the specific recommendation. For example, whereas an item of information may be accorded a certain score generally, the item may be more important in view of a specific preventive care service recommendation and, thus, may be scored accordingly. As indicated by step 1012, it may be determined whether the reliability of the recommendation needs improvement. If not, the process may end. If so, a healthcare provider may be prompted to seek information needed to improve the reliability of the recommendation, as indicated at step 1014. In alternative or in combination, one or more data source(s) may be accessed to seek information needed to improve the reliability of the recommendation, as indicated at step 1016.

Figure 11:
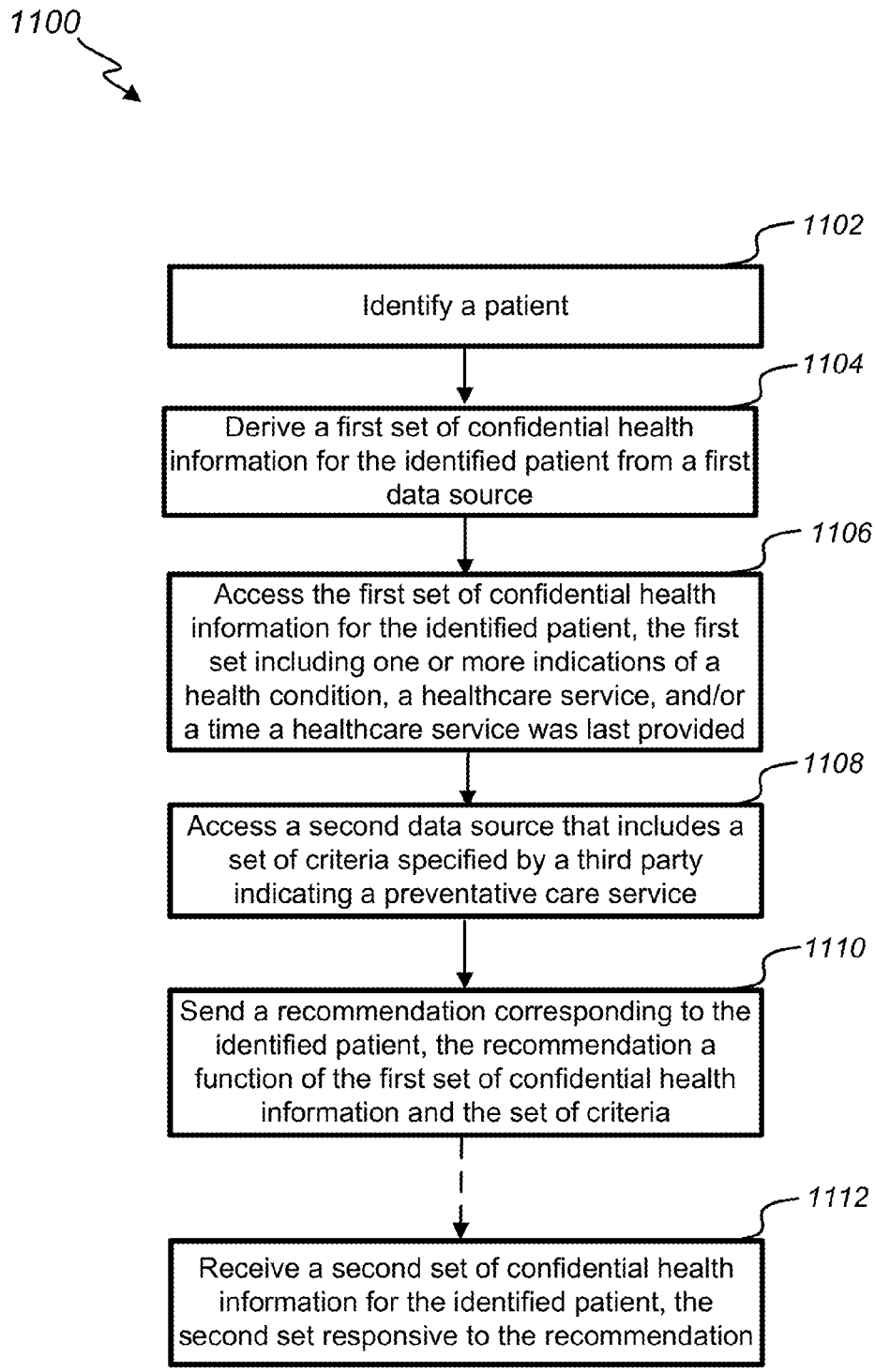
FIG. 11 illustrates a method for providing a preventative care recommendation corresponding to a patient, in accordance with certain embodiments of the present disclosure.

FIG. 11 illustrates a method 1100 for providing a preventative care recommendation corresponding to a patient, in accordance with certain embodiments of the present disclosure. According to one embodiment, the method 1100 may begin at step 1102. The preventative care recommendation process may be responsive to a request. In some embodiments, the preventative care recommendation process may be initiated by a healthcare provider; in some embodiments, the preventative care recommendation process may be initiated by another user such as the patient. At step 1102, a patient may be identified. The preventative care recommendation process may be automatically initiated, for example, based on a set schedule or on an event such as a new information update.

As indicated by step 1104, a first set of confidential health information for the identified patient may be derived from a first data source. By way of non-limiting example, first set of confidential health information for the identified patient may be pulled and/or pushed from healthcare providers/payers/data sources or may be pre-loaded and/or otherwise directly transferred. As indicated by step 1106, the first set of confidential health information for the identified patient may be accessed. For non-limiting example, the first set of confidential health information may be retrieved from one or more health repositories such as database(s)/memory(ies). The first set may include any suitable confidential health information for the identified patient. The first set may include, without limitation, one or more indications of a health condition, a healthcare service, and/or a time a healthcare service was last provided to the identified patient.

As indicated by step 1108, a second data source may be accessed. The second data source may include a set of criteria specified by a third party indicating a preventative care service. In certain embodiments, the third party may correspond to a healthcare payer, and the criteria may be specified by the healthcare payer. The criteria may indicate whether one or more preventive care services are eligible for payment by the payer, and the indication of eligibility may be specific to the identified patient. The recommendation may be tailored for a healthcare provider of the patient in some embodiments. In some embodiments, the recommendation may be tailored for the patient. The recommendation may be a function, at least in part, of the first set of confidential health information and the set of criteria. As indicated by step 1110, a recommendation corresponding to the identified patient may be sent. In various embodiments, the recommendation may be sent to the patient and/or the patient's healthcare provider. As indicated by step 1112, in some instances, a second set of confidential health information for the identified patient may be received, the second set being responsive to the recommendation that was previously sent. The responsive information may be taken into account, in conjunction with the first set of confidential health information, the other information previously processed, and a second recommendation may be generated and sent to the patient and/or healthcare provider.

Figure 12:
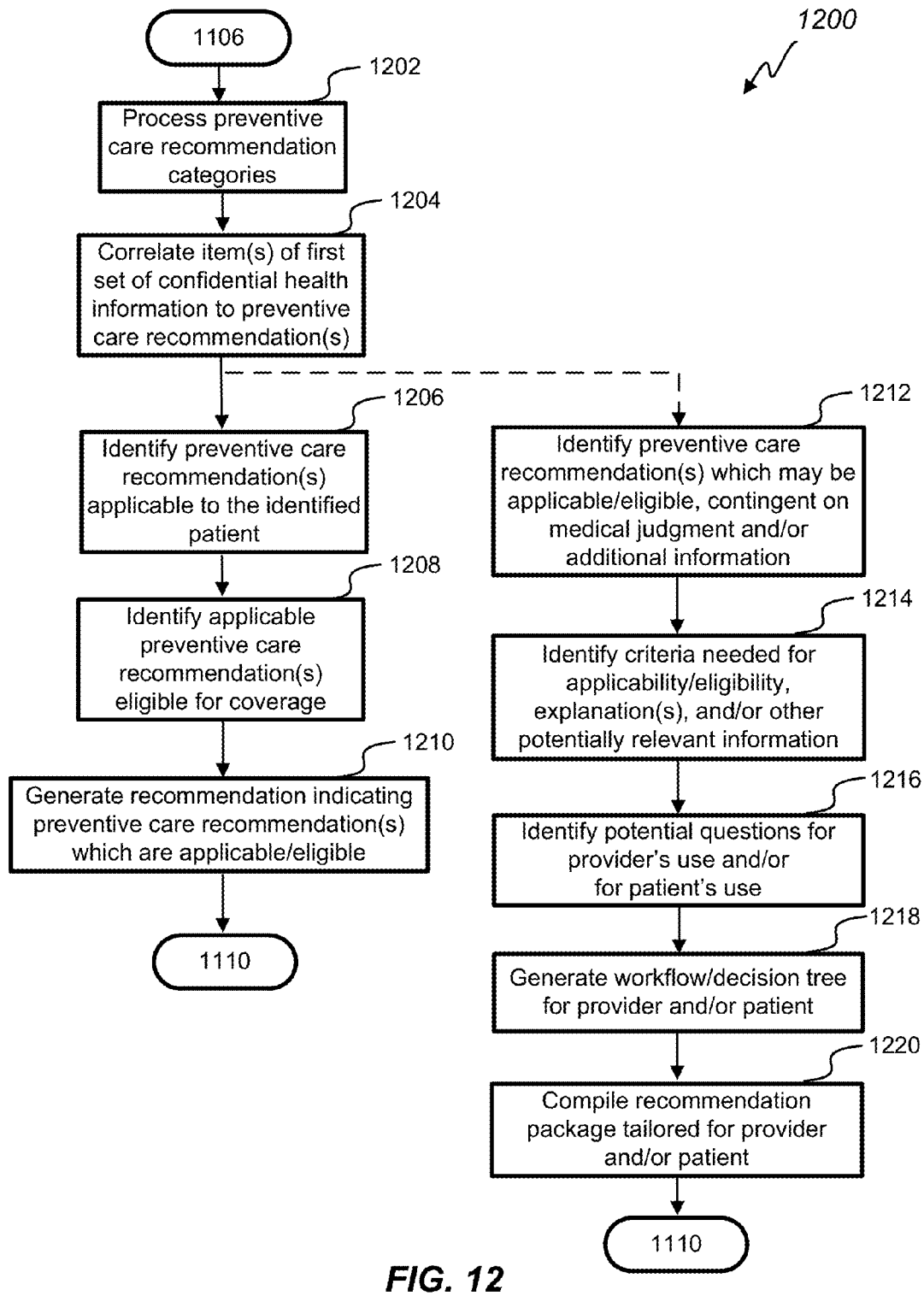
FIG. 12 illustrates a method for generating a preventative care recommendation corresponding to a patient, in accordance with certain embodiments of the present disclosure.

FIG. 12 illustrates a method 1200 for generating a preventative care recommendation corresponding to a patient, in accordance with certain embodiments of the present disclosure. Teachings of the present disclosure may be implemented in a variety of configurations that may correspond to the systems disclosed herein. As such, certain steps of the method 1200 may be omitted, and the order of the steps may be shuffled in any suitable manner and may depend on the implementation chosen. Moreover, while the following steps may be separated for the sake of description, it should be understood that certain steps may be performed simultaneously or substantially simultaneously.

One non-limiting example of the method 1200 may begin with a transition from step 1106 of the method 1100 to step 1202 of the method 1200. As indicated by step 1202, preventive care recommendation categories may be processed. The possible preventive care recommendations and categories may be taken into account, and data regarding the preventive care recommendations and categories may be prepared for correlating to the confidential health information of the patient. In certain embodiments, the categorization may include one or more of the following non-limiting examples. Categorization based at least in part on the Task Force letter grade, (such as A, B, C, etc.) may be taken into account. Certain recommendations may be categorized based at least in part on the sex of the patient. Certain recommendations may be categorized based at least in part on the age of the patient. Certain recommendations may be categorized based at least in part on certain activities of the patient (e.g., smoking, sexual activity, etc.). Certain recommendations may be categorized based at least in part on certain conditions of the patient (e.g., pregnancy, blood type).

Certain categories may be eliminated as not being applicable to the patient. For example, prevent care recommendations specific to women could be eliminated for a male patient, prevent care recommendations specific to pregnant women could be eliminated for a non-pregnant female patient, etc. Additionally, certain categories may be identified as of particular relevance to the patient, for example, based on a history of the patient previously retained. For example, diabetes may be prevalent in the patient's family history, and, thus, diabetes screening may be identified as of particular relevance to the patient.

As indicated by step 1204, item(s) of first set of confidential health information may be correlated to preventive care recommendation(s). Items of confidential health information of the patient may be compared to details of the preventive care recommendations to determine which recommendations are applicable to the patient (e.g., calendar-based recommendations, which may correspond to certain Grade A/B recommendations of the Task Force) and which recommendations may be applicable to the patient depending on medical judgment of a healthcare provider tending to the patient and/or depending on additional information that is needed to make the determination. Thus, as indicated by step 1206, preventive care recommendation(s) applicable to the patient may be identified; and, as indicated by step 1212, preventive care recommendation(s) which may be applicable/eligible, contingent on medical judgment and/or additional information, may be identified.

As indicated by step 1208, applicable preventive care recommendation(s) eligible for coverage by a healthcare payer may be identified. While current law requires insurance plans to cover specific preventive services (such as certain Grade A/B recommendations), with respect to other services, the payer may have reimbursement guidelines that might specify coverage qualifications and requirements. As indicated by step 1210, a recommendation indicating preventive care recommendation(s) which are applicable/eligible may be generated.

As indicated by step 1214, criteria needed for applicability/eligibility, explanation(s), and/or other potentially relevant information may be identified, generated, gathered, and/or organized. The payer may have reimbursement guidelines that might specify what qualifying information needed in order to determine services for which the payer will provide payment. As indicated by step 1216, potential questions for provider's use and/or for patient's use may be identified, generated, gathered, and/or organized. As indicated by step 1218, a workflow and/or decision tree for the provider and/or patient may be identified and/or generated. As indicated by step 1220, recommendation package tailored for the provider and/or patient may be compiled. Then, the process flow may transition to step 1110 of the method 1100.

Figure 13:
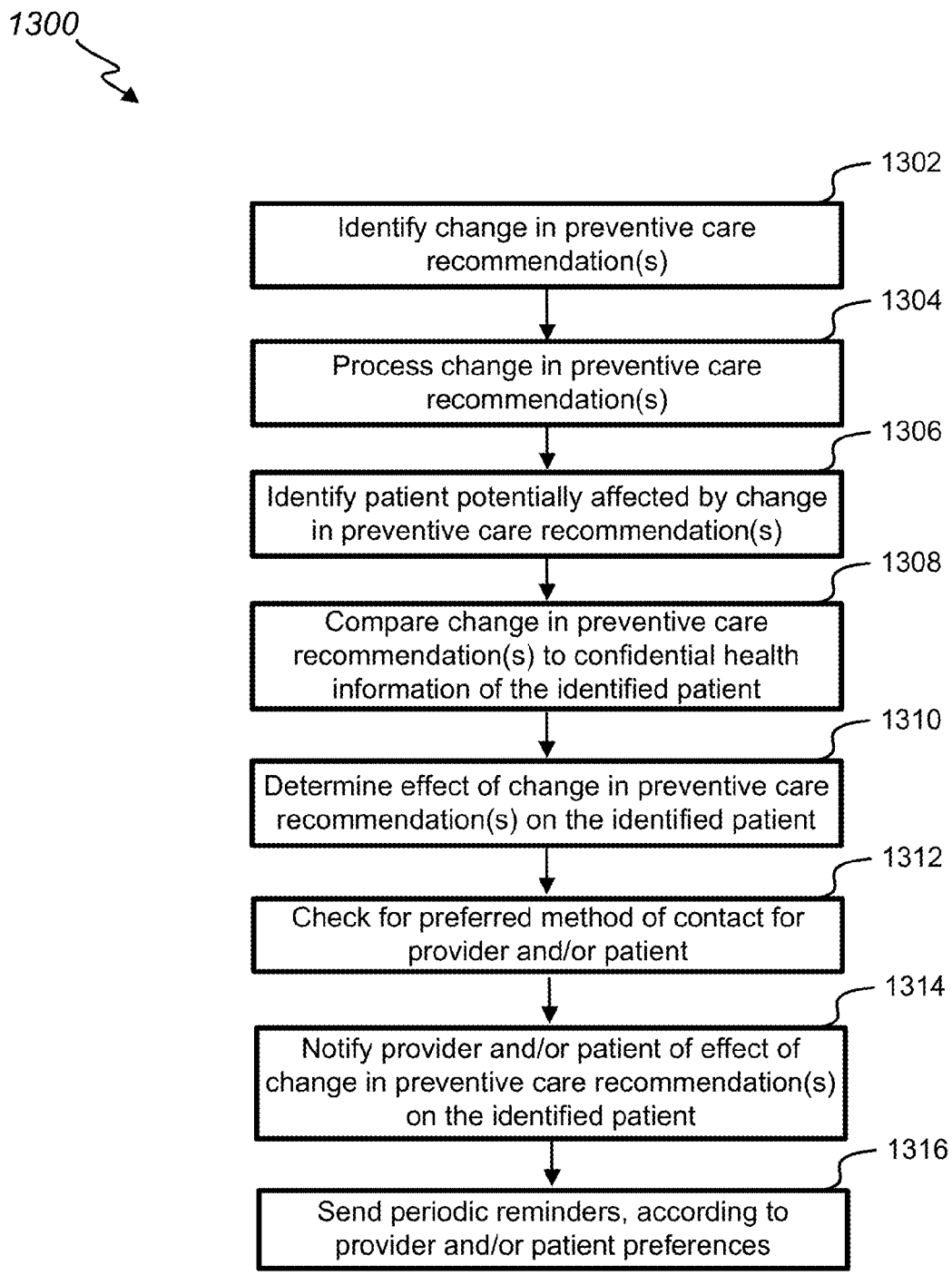
FIG. 13 illustrates a method for handling changes in preventive care recommendations, in accordance with certain embodiments of the present disclosure.

FIG. 13 illustrates a method 1300 for handling changes in preventive care recommendations, in accordance with certain embodiments of the present disclosure. Certain steps of the method 1300 may be omitted, and the order of the steps may be shuffled in any suitable manner and may depend on the implementation chosen. Moreover, while the following steps may be separated for the sake of description, it should be understood that certain steps may be performed simultaneously or substantially simultaneously. The preventive care recommendations may correspond to those issued by the Task Force and/or implemented by law/regulation. However, the preventive care recommendations may correspond to any guidelines/laws/regulations/rules issued by an authority, be it government or otherwise, relating to preventive care.

One non-limiting example of the method 1300 may begin with a step 1302. As indicated by step 1302, one or more changes in preventive care recommendation(s) may be identified. The identification may be made by way of linking to a site that provides updates on such changes, periodically crawling sites for updates and changes, and/or otherwise receiving notice of changes in the guidelines. As indicated by step 1304, the changes in preventive care recommendations may be processed. The scope of the changes may be identified. For non-limiting example, it may be determined that the changes affect certain preventive services, certain types of patients, certain payers, etc. Potential ramifications may be identified. For non-limiting example, it may be determined that the changes translate to greater or lesser thresholds for preventive care service applicability to certain patients and/or eligibility for cost-sharing by payers. Data, regarding details, scope, extent, and/or potential ramifications of the changes, may be prepared for correlating to the confidential health information of particular patients.

As indicated by step 1306, a patient potentially affected by the change(s) in preventive care recommendation(s) may be identified. The identification of the patient may be based on the determinations that the changes affect certain preventive services, certain types of patients, certain payers, etc., and correlating those determinations with the patient. As indicated by step 1308, changes in preventive care recommendations may be compared to confidential health information of the identified patient. The comparison may consider, for non-limiting example, that past recommendations, treatments/tests/therapies, etc. in order to correct any out-of-date information or recommendations. The comparison may consider threshold conditions of the patient, such as age thresholds (e.g., a service is recommended after the patient reaches a particular age), frequency thresholds (e.g., a service is recommended annually), and the like, that may affect when the patient is due for a particular preventive care service. In the case of a newly recommended service, it may be determined whether the patient has already received the service.

As indicated by step 1310, effects of the changes in preventive care recommendations on the identified patient may be determined. The effects may be revealed as a result of the previous comparisons. The effects may be compiled and formatted for communication to the patient. As indicated by step 1312, there may be a check for a preferred method of contact for the provider and/or patient. A healthcare provider or patient, having previously set up an account, may have specified a preferred method, whether it be text, voice, e-mail, or paper mail. In that way, those that are affected by the changes may be promptly notified. As indicated by step 1314, the patient and/or the patient's provider may be notified of the effects of changes in preventive care recommendation(s) on the identified patient. As indicated by step 1316, periodic reminders may be sent according to the provider and/or patient preferences.

Figure 14:
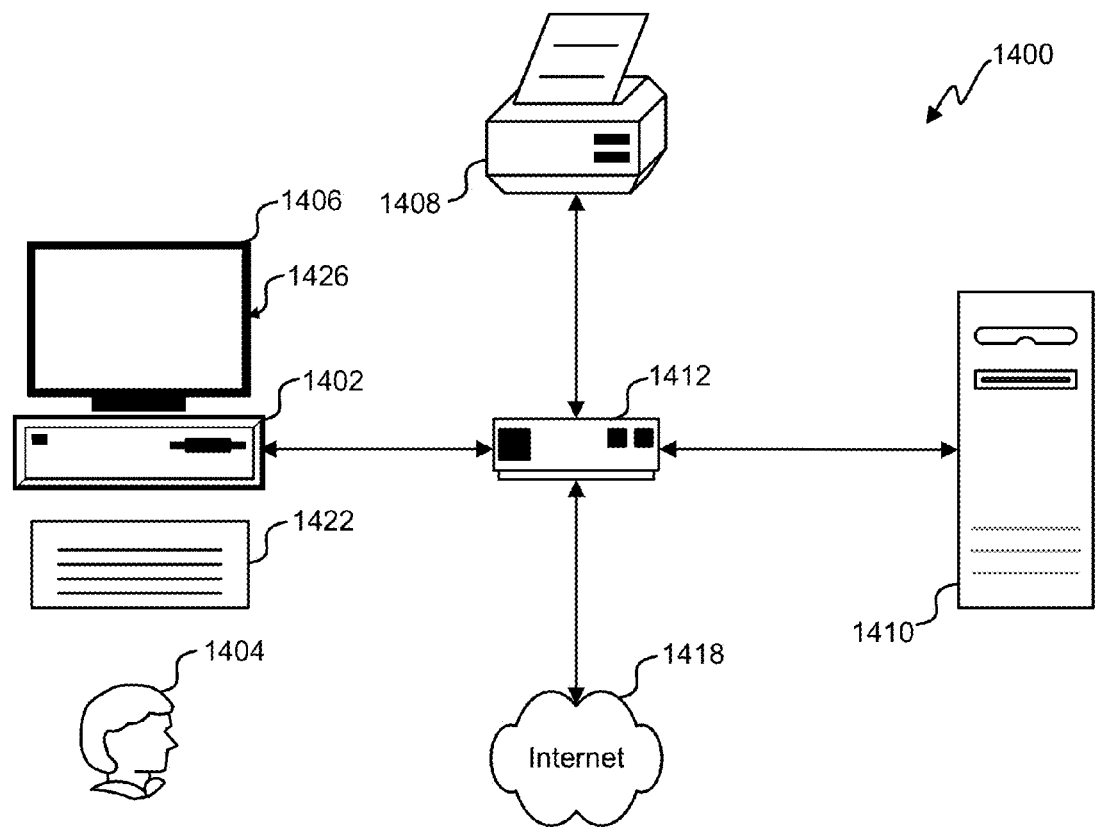
FIG. 14 depicts a block diagram of an embodiment of a computer system, in accordance with certain embodiments of the present disclosure.

Referring next to FIG. 14, an exemplary environment with which embodiments may be implemented is shown with a computer system 1400 that can be used by a designer 1404 to design, for example, electronic designs. The computer system 1400 can include a computer 1402, keyboard 1422, a network router 1412, a printer 1408, and a monitor 1406. The monitor 1406, processor 1402 and keyboard 1422 are part of a computer system 1426, which can be a laptop computer, desktop computer, handheld computer, mainframe computer, etc. The monitor 1406 can be a CRT, flat screen, etc.

A designer 1404 can input commands into the computer 1402 using various input devices, such as a mouse, keyboard 1422, track ball, touch screen, etc. If the computer system 1400 comprises a mainframe, a designer 1404 can access the computer 1402 using, for example, a terminal or terminal interface. Additionally, the computer system 1426 may be connected to a printer 1408 and a server 1410 using a network router 1412, which may connect to the Internet 1418 or a WAN.

The server 1410 may, for example, be used to store additional software programs and data. In one embodiment, software implementing the systems and methods described herein can be stored on a storage medium in the server 1410. Thus, the software can be run from the storage medium in the server 1410. In another embodiment, software implementing the systems and methods described herein can be stored on a storage medium in the computer 1402. Thus, the software can be run from the storage medium in the computer system 1426. Therefore, in this embodiment, the software can be used whether or not computer 1402 is connected to network router 1412. Printer 1408 may be connected directly to computer 1402, in which case, the computer system 1426 can print whether or not it is connected to network router 1412.

Figure 15:
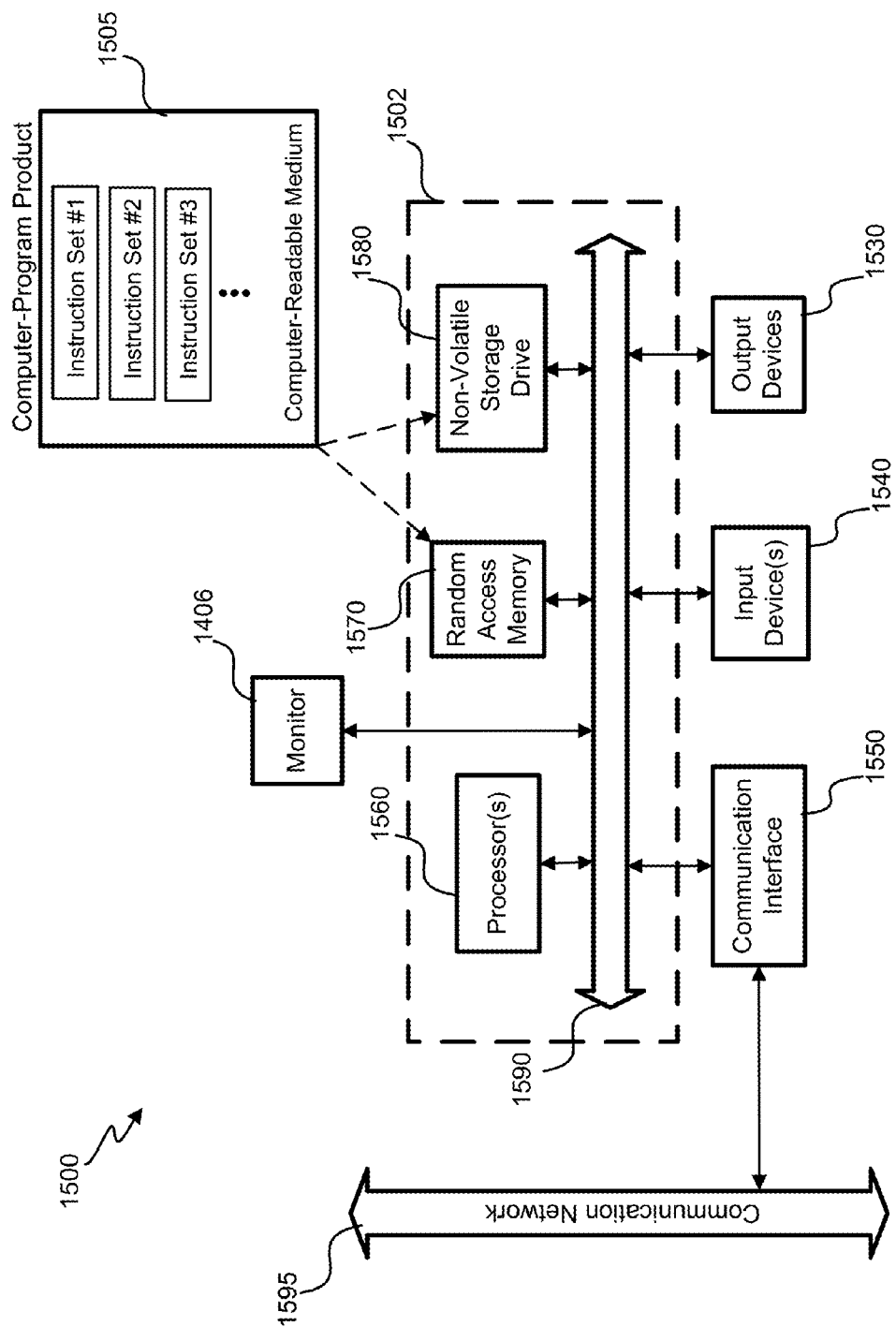
FIG. 15 depicts a block diagram of an embodiment of a special-purpose computer system, in accordance with certain embodiments of the present disclosure.

With reference to FIG. 15, an embodiment of a special-purpose computer system 104 is shown. The above methods may be implemented by computer-program products that direct a computer system to perform the actions of the above-described methods and components. Each such computer-program product may comprise sets of instructions (codes) embodied on a computer-readable medium that directs the processor of a computer system to perform corresponding actions. The instructions may be configured to run in sequential order, or in parallel (such as under different processing threads), or in a combination thereof. After loading the computer-program products on a general purpose computer system 1426, it is transformed into the special-purpose computer system 104.

Special-purpose computer system 104 comprises a computer 1402, a monitor 1406 coupled to computer 1402, one or more additional user output devices 1530 (optional) coupled to computer 1402, one or more user input devices 1540 (e.g., keyboard, mouse, track ball, touch screen) coupled to computer 1402, an optional communications interface 1550 coupled to computer 1402, a computer-program product 1505 stored in a tangible computer-readable memory in computer 1402. Computer-program product 1505 directs system 104 to perform the above-described methods. Computer 1402 may include one or more processors 1560 that communicate with a number of peripheral devices via a bus subsystem 1590. These peripheral devices may include user output device(s) 1530, user input device(s) 1540, communications interface 1550, and a storage subsystem, such as random access memory (RAM) 1570 and non-volatile storage drive 1580 (e.g., disk drive, optical drive, solid state drive), which are forms of tangible computer-readable memory.

Computer-program product 1505 may be stored in non-volatile storage drive 1580 or another computer-readable medium accessible to computer 1402 and loaded into memory 1570. Each processor 1560 may comprise a microprocessor, such as a microprocessor from Intel® or Advanced Micro Devices, Inc.®, or the like. To support computer-program product 1505, the computer 1402 runs an operating system that handles the communications of product 1505 with the above-noted components, as well as the communications between the above-noted components in support of the computer-program product 1505. Exemplary operating systems include Windows® or the like from Microsoft® Corporation, Solaris® from Oracle®, LINUX, UNIX, and the like.

User input devices 1540 include all possible types of devices and mechanisms to input information to computer system 1402. These may include a keyboard, a keypad, a mouse, a scanner, a digital drawing pad, a touch screen incorporated into the display, audio input devices such as voice recognition systems, microphones, and other types of input devices. In various embodiments, user input devices 1540 are typically embodied as a computer mouse, a trackball, a track pad, a joystick, wireless remote, a drawing tablet, a voice command system. User input devices 1540 typically allow a user to select objects, icons, text and the like that appear on the monitor 1406 via a command such as a click of a button or the like. User output devices 1530 include all possible types of devices and mechanisms to output information from computer 1402. These may include a display (e.g., monitor 1406), printers, non-visual displays such as audio output devices, etc.

Communications interface 1550 provides an interface to other communication networks and devices and may serve as an interface to receive data from and transmit data to other systems, WANs and/or the Internet 1418. Embodiments of communications interface 1550 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 1550 may be coupled to a computer network, to a FireWire® bus, or the like. In other embodiments, communications interface 1550 may be physically integrated on the motherboard of computer 1402, and/or may be a software program, or the like.

RAM 1570 and non-volatile storage drive 1580 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1570 and non-volatile storage drive 1580 may be configured to store the basic programming and data constructs that provide the functionality of various embodiments of the present invention, as described above.

Software instruction sets that provide the functionality of the present invention may be stored in RAM 1570 and non-volatile storage drive 1580. These instruction sets or code may be executed by the processor(s) 1560. RAM 1570 and non-volatile storage drive 1580 may also provide a repository to store data and data structures used in accordance with the present invention. RAM 1570 and non-volatile storage drive 1580 may include a number of memories including a main random access memory (RAM) to store of instructions and data during program execution and a read-only memory (ROM) in which fixed instructions are stored. RAM 1570 and non-volatile storage drive 1580 may include a file storage subsystem providing persistent (non-volatile) storage of program and/or data files. RAM 1570 and non-volatile storage drive 1580 may also include removable storage systems, such as removable flash memory.

Bus subsystem 1590 provides a mechanism to allow the various components and subsystems of computer 1402 communicate with each other as intended. Although bus subsystem 1590 is shown schematically as a single bus, alternative embodiments of the bus subsystem may utilize multiple busses or communication paths within the computer 1402.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A preventative care recommendation engine to provide a preventative care recommendation corresponding to a patient, the preventative care engine comprising:
   one or more network interfaces accessible by one or more of a healthcare provider and/or a patient;
   one or more processors, coupled to the one or more network interfaces, to execute instructions to:
      access a set of confidential health information for an identified patient, wherein the set of confidential health information for the identified patient:
         is derived from a first data source; and
         includes one or more of:
            an indication of a health condition of the identified patient;
            an indication of a healthcare service provided to the identified patient; and/or
            an indication of a time when the health care service was provided to the identified patient;
      access a second data source that includes a set of criteria specified by a third party indicating eligibility of a preventative care service for payment by the third party; and
      send a recommendation corresponding to the identified patient, wherein the recommendation is a function of:
         the set of confidential health information for the identified patient;
         the indication of the healthcare service provided to the identified patient;
         the indication of the time when the health care service was provided to the identified patient; and
         the set of criteria specified by the third party indicating eligibility of the preventative care service for payment by the third party;
      wherein the indication of time is used in determining applicability of the preventive care service at least partially based on whether an amount of time since the healthcare service was provided to the identified patient meets a time-based threshold; and
      wherein the recommendation comprises an indication of a workflow corresponding to a decision tree for the healthcare provider and/or the identified patient, wherein the workflow:
         distinguishes one or more potential preventive care services that are applicable to the identified patient contingent on medical judgment and/or additional information that is needed; and
         identifies one or more steps to take in determining whether the one or more potential preventive care services ultimately apply to the identified patient based at least in part on the medical judgment and/or the additional information; and
   one or more storage media coupled to the one or more processors to retain the instructions.

2. The preventative care recommendation engine of claim 1, wherein the recommendation further comprises an indication of eligibility of the preventive care service for payment by the third party.

3. The preventative care recommendation engine of claim 1, wherein the one or more processors are to execute further instructions to:
   receive a second set of confidential health information for the identified patient, wherein the second set of confidential health information for the identified patient is based, at least in part, on the recommendation.

4. The preventative care recommendation engine of claim 1, wherein the healthcare provider corresponds to a physician associated with the identified patient.

5. A method to provide a preventative care recommendation corresponding to a patient, the method comprising:
accessing, by a computer system, a set of confidential health information for an identified patient, wherein the set of confidential health information:
is derived from a first data source; and
includes one or more of:
an indication of a health condition of the identified patient;
an indication of a healthcare service provided to the identified patient; and/or
an indication of a time when the health care service was provided to the identified patient;
accessing, by the computer system, a second data source that includes a set of criteria specified by a third party indicating eligibility of a preventative care service for payment by the third party;
sending, by the computer system, a recommendation corresponding to the identified patient, wherein the recommendation is a function of:
the set of confidential health information for the identified patient;
the indication of the healthcare service provided to the identified patient;
the indication of the time when the health care service was provided to the identified patient; and
the set of criteria specified by the third party indicating eligibility of the preventative care service for payment by the third party;
wherein the indication of time is used in determining applicability of the preventive care service at least partially based on whether an amount of time since the healthcare service was provided to the identified patient meets a time-based threshold; and
wherein the recommendation comprises an indication of a workflow corresponding to a decision tree for the healthcare provider and/or the identified patient, wherein the workflow:
distinguishes one or more potential preventive care services that are applicable to the identified patient contingent on medical judgment and/or additional information that is needed; and
identifies one or more steps to take in determining whether the one or more potential preventive care services ultimately apply to the identified patient based at least in part on the medical judgment and/or the additional information.

6. The method of claim 5, wherein the recommendation further comprises an indication of eligibility of the preventive care service for payment by the third party.

7. The method of claim 5, further comprising:
receiving a second set of confidential health information for the identified patient, wherein the second set of confidential health information for the identified patient is based, at least in part, on the recommendation.

8. The method of claim 5, wherein the healthcare provider corresponds to a physician associated with the identified patient.

9. One or more non-transitory machine-readable media having machine-readable instructions thereon which, when executed by one or more processors, implements a method provide a preventative care recommendation corresponding to a patient, the method comprising:
accessing a set of confidential health information for an identified patient, wherein the set of confidential health information:
is derived from a first data source; and
includes one or more of:
an indication of a health condition of the identified patient;
an indication of a healthcare service provided to the identified patient; and/or
an indication of a time when the health care service was provided to the identified patient;
accessing a second data source that includes a set of criteria specified by a third party indicating eligibility of a preventative care service for payment by the third party;
sending a recommendation corresponding to the identified patient, wherein the recommendation is a function of:
the set of confidential health information for the identified patient;
the indication of the healthcare service provided to the identified patient;
the indication of the time when the health care service was provided to the identified patient; and
the set of criteria specified by the third party indicating eligibility of the preventative care service for payment by the third party;
wherein the indication of time is used in determining applicability of the preventive care service at least partially based on whether an amount of time since the healthcare service was provided to the identified patient meets a time-based threshold; and
wherein the recommendation comprises an indication of a workflow corresponding to a decision tree for the healthcare provider and/or the identified patient, wherein the workflow:
distinguishes one or more potential preventive care services that are applicable to the identified patient contingent on medical judgment and/or additional information that is needed; and
identifies one or more steps to take in determining whether the one or more potential preventive care services ultimately apply to the identified patient based at least in part on the medical judgment and/or the additional information.

10. The one or more non-transitory machine-readable media of claim 9, wherein the recommendation further comprises an indication of eligibility of the preventive care service for payment by the third party.

11. The one or more non-transitory machine-readable media of claim 9, wherein the method further comprises:
receiving a second set of confidential health information for the identified patient, wherein the second set of confidential health information for the identified patient is based, at least in part, on the recommendation.

* * * * *